United States Patent
Chen et al.

(10) Patent No.: US 8,367,633 B2
(45) Date of Patent: Feb. 5, 2013

(54) METHODS OF TREATING B-CELL CANCERS

(75) Inventors: Luojing Chen, Rochester, NY (US); Jiyong Zhao, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 12/672,088

(22) PCT Filed: Aug. 6, 2008

(86) PCT No.: PCT/US2008/072330
§ 371 (c)(1),
(2), (4) Date: Mar. 18, 2010

(87) PCT Pub. No.: WO2009/021034
PCT Pub. Date: Feb. 12, 2009

(65) Prior Publication Data
US 2011/0070240 A1    Mar. 24, 2011

Related U.S. Application Data

(60) Provisional application No. 60/954,246, filed on Aug. 6, 2007.

(51) Int. Cl.
*A61K 48/00* (2006.01)

(52) U.S. Cl. ...... 514/44; 536/24.5; 536/24.31; 536/24.1

(58) Field of Classification Search ........................ None
See application file for complete search history.

(56) References Cited

U.S. PATENT DOCUMENTS

| | | |
|---|---|---|
| 2005/0182006 A1 | 8/2005 | McSwiggen et al. |
| 2006/0160762 A1 | 7/2006 | Zetter et al. |
| 2006/0247199 A1 | 11/2006 | Newell |

FOREIGN PATENT DOCUMENTS

| | | |
|---|---|---|
| WO | 9955865 A1 | 11/1999 |

OTHER PUBLICATIONS

Meylan et al.( EMBO 2002, vol. 3: 1201-1208).*
PCT International Search Report and Written Opinion PCT/US2008/072330 (Feb. 2, 2009).
Cariappa et al., J. Immunology 171:1875-1880 (2003).
Moran et al., Molecular Immunology 43:1694-1699 (2006).

* cited by examiner

*Primary Examiner* — Kimberly Chong
(74) *Attorney, Agent, or Firm* — LeClairRyan, a Professional Corporation

(57) ABSTRACT

The present invention is directed to methods of causing malignant B-cells and treating malignant B-cells. These methods involve the use of an inhibitor of PKK activity, whether active directly against PKK or effective to knockdown PKK expression, which when introduced into a malignant B cell (or administered to a patient) is effective to cause cell death of the malignant B cell, thereby treating the B-cell malignancy.

10 Claims, 12 Drawing Sheets

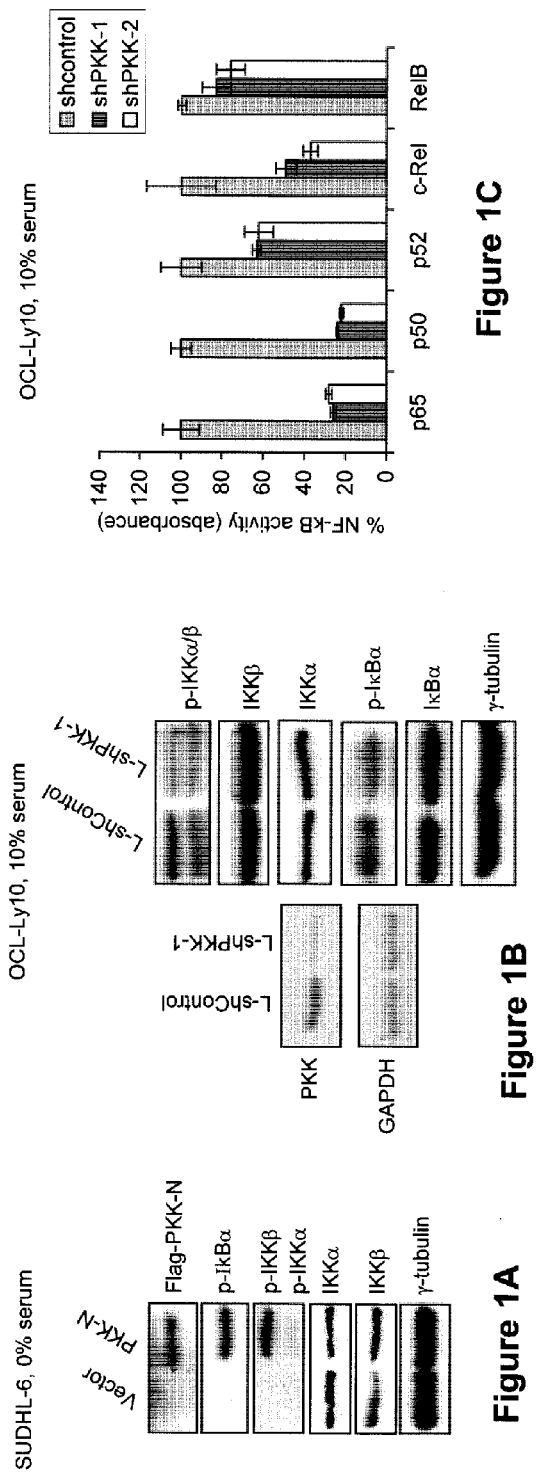
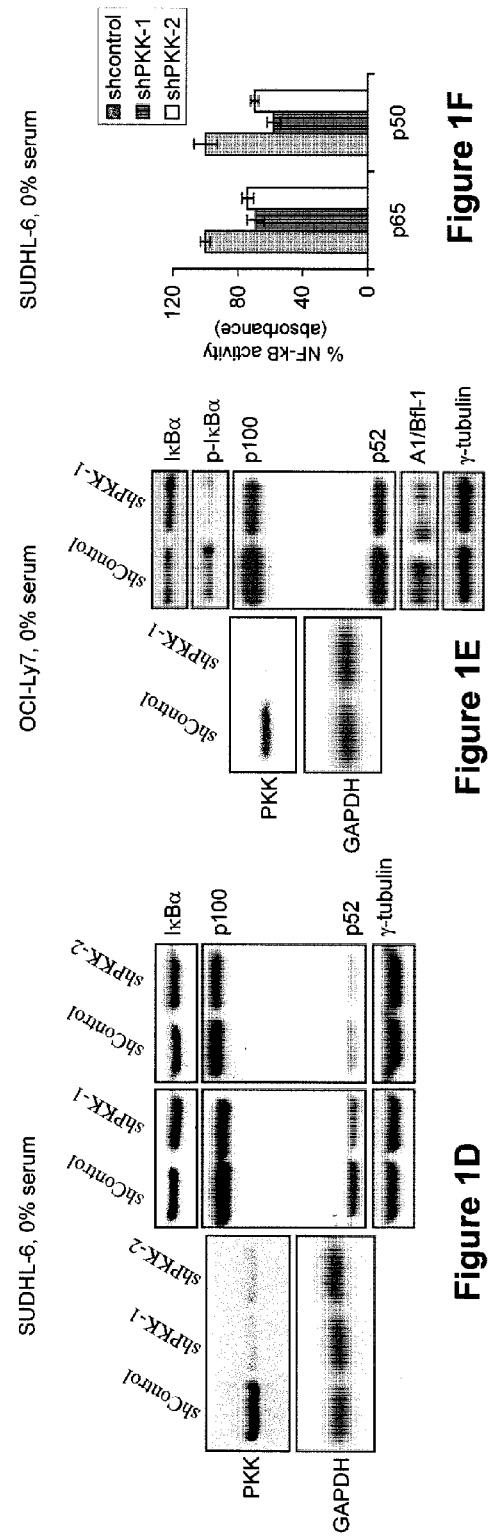
Figure 1A
Figure 1B
Figure 1C
Figure 1D
Figure 1E
Figure 1F

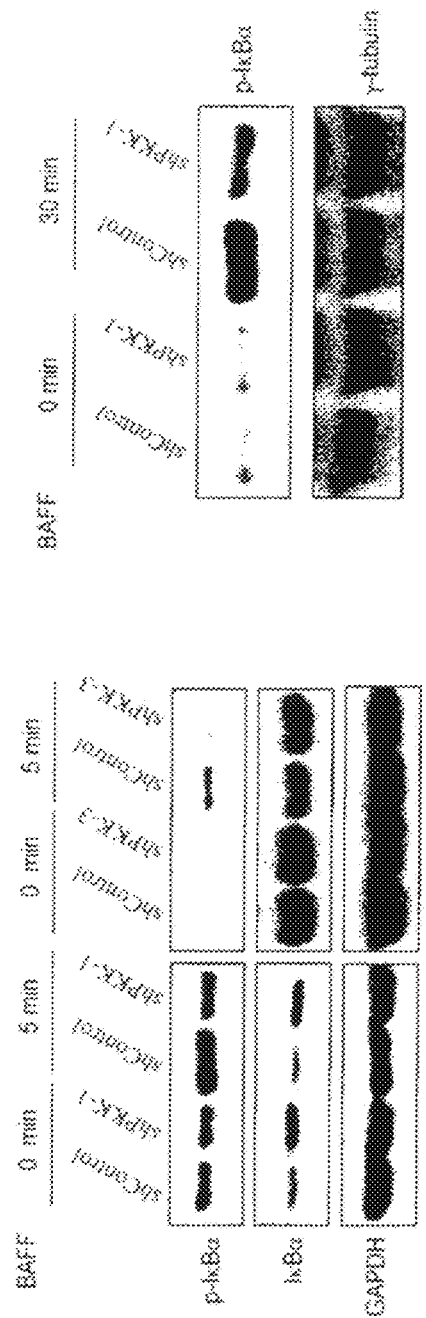

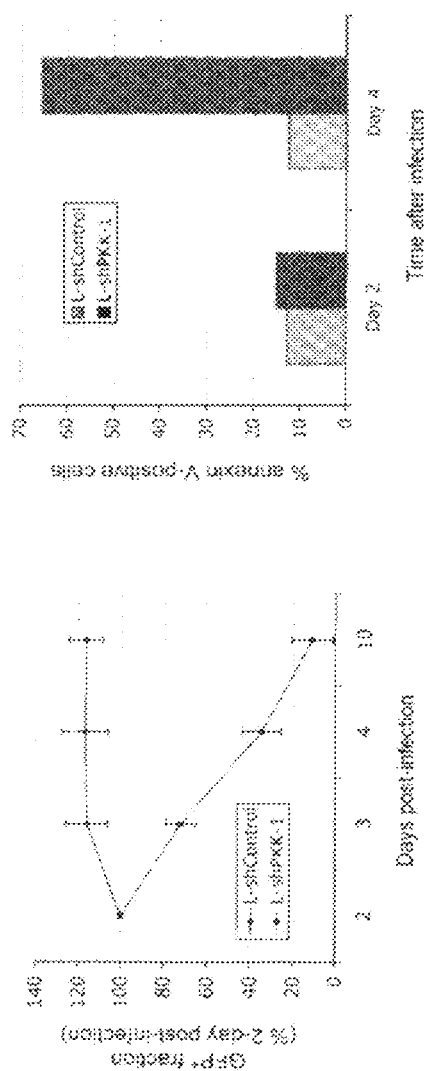
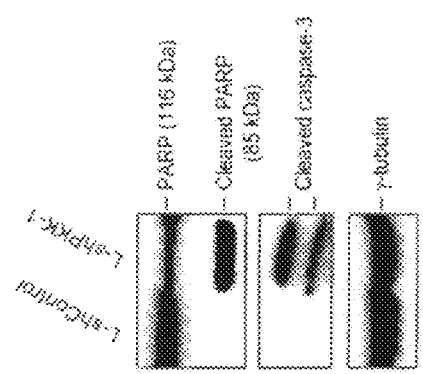
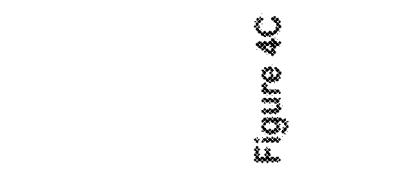
Figure 4A
Figure 4B
Figure 4C

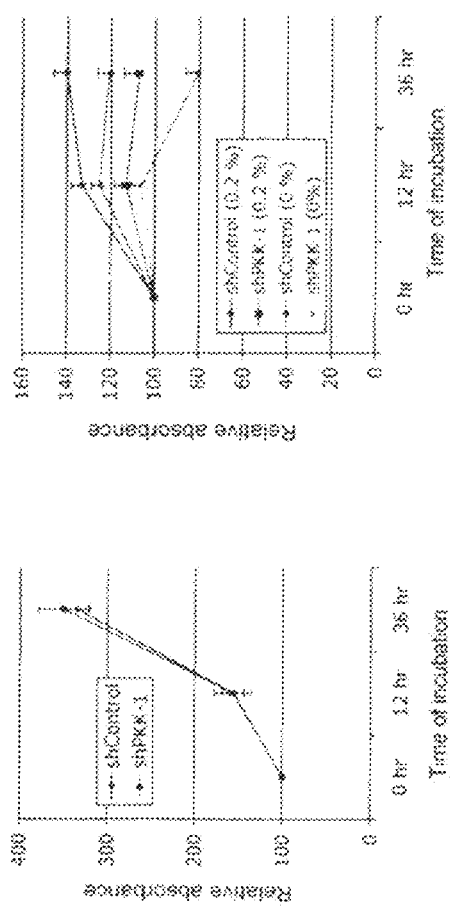
Figure 6A
Figure 6B
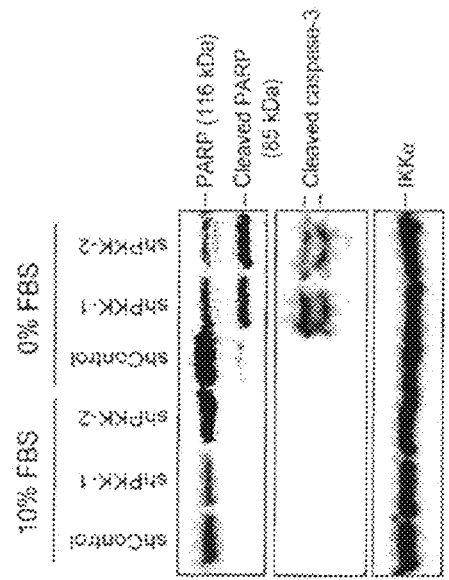
Figure 6C
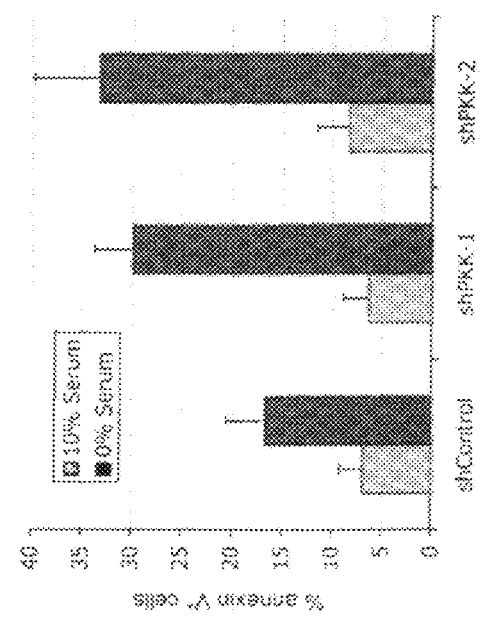
Figure 6D

METHODS OF TREATING B-CELL CANCERS

This application is a national stage application under 35 U.S.C. 371 of PCT/US2008/072330 filed Aug. 6, 2008, and claims the benefit of U.S. Provisional Patent Application Ser. No. 60/954,246, filed Aug. 6, 2007, which is hereby incorporated by reference in its entirety.

FIELD OF THE INVENTION

The present invention is directed to methods of treating B cell cancers and auto-immune disease, particularly through the disruption of protein kinase C-associated kinase ("PKK," also known as DIK and RIP-4), which is required for NF-κB signaling and survival of lymphoma cells and myeloma cells, but not healthy B cells.

BACKGROUND OF THE INVENTION

B cells are a critical component of the immune response in mammals, as they are the cells responsible for antibody production (humoral immunity). Each B cell within the host expresses a different antibody—thus, one B cell will express antibody specific for one antigen, while another B cell will express antibody specific for a different antigen. Accordingly, B cells are quite diverse, and this diversity is critical to the immune system. In humans, each B cell can produce an enormous number of antibody molecules (i.e., about $10^7$ to $10^8$). The maturation of B cells (and thus antibody production) most typically ceases or substantially decreases when the foreign antigen has been neutralized. Occasionally, however, proliferation of a particular B cell or plasma cell will continue unabated; such proliferation can result in a cancer referred to as "B cell lymphoma or multiple myeloma."

B cell lymphomas include both Hodgkin's lymphoma and a broad class of non-Hodgkin's lymphoma. Non-Hodgkin's lymphoma encompasses over 29 types of lymphoma. The distinctions are based on the type of cancer cells, and often the cancers are classified by cell type and rate of growth.

The incidence of non-Hodgkin's lymphoma is much greater than the incidence of Hodgkin's lymphoma: about 8 in 9 cases. According to the American Cancer Society, an estimated 54,000 new non-Hodgkin's lymphoma cases will be diagnosed, 65% of which will be classified as intermediate- or high-grade lymphoma. Patients diagnosed with intermediate-grade lymphoma have an average survival rate of two to five years, and patients diagnosed with high-grade lymphoma survive an average of six months to two years after diagnosis.

Diffuse large B cell lymphoma (DLBCL) is an aggressive and the most common subtype of non-Hodgkin's lymphoma, accounting for 30-40% of lymphoid malignancy. Although DLBCL represents one of the most therapy-responsive malignancies, only approximately 40% of the patients can be cured by the current treatments with multiple therapeutic agents (Abramson et al., "Advances in the Biology and Therapy of Diffuse Large B-cell Lymphoma: Moving Toward a Molecularly Targeted Approach," *Blood* 106:1164-1174 (2005); Staudt et al., "The Biology of Human Lymphoid Malignancies Revealed by Gene Expression Profiling," *Adv Immunol* 87:163-208 (2005)). As a result, nearly 10,000 patients die from DLBCL each year in the United States, (Staudt et al., "The Biology of Human Lymphoid Malignancies Revealed by Gene Expression Profiling," *Adv Immunol* 87:163-208 (2005)), underscoring the importance of better molecular understanding of DLBCL and identifying proper therapeutic targets. Based on gene expression profiles, DLBCL can be divided into at least three subgroups: activated B cell-like (ABC) DLBCL, germinal center B cell-like (GCB) DLBCL, and primary mediastinal B cell lymphoma (PMBL), with the ABC and PMBL subgroups exhibiting higher levels of expression of NF-κB target genes than the GCB subgroup (Rosenwald et al., "Molecular Diagnosis of Primary Mediastinal B Cell Lymphoma Identifies a Clinically Favorable Subgroup of Diffuse Large B Cell Lymphoma Related to Hodgkin Lymphoma," *J Exp Med* 198:851-862 (2003); Wright et al., "A Gene Expression-based Method to Diagnose Clinically Distinct Subgroups of Diffuse Large B Cell Lymphoma," *Proc Natl Acad Sci USA* 100:9991-9996 (2003); Alizadeh et al., "Distinct Types of Diffuse Large B-cell Lymphoma Identified by Gene Expression Profiling," *Nature* 403:503-511 (2000); Savage et al., "The Molecular Signature of Mediastinal Large B-cell Lymphoma Differs from That of Other Diffuse Large B-cell Lymphomas and Shares Features with Classical Hodgkin Lymphoma," *Blood* 102:3871-3879 (2003)). It was shown that constitutive NF-κB signaling is required for survival of ABC and PMBL DLBCL cells (Feuerhake et al., "NFκB Activity, Function, and Target-gene Signatures in Primary Mediastinal Large B-cell Lymphoma and Diffuse Large B-cell Lymphoma Subtypes," *Blood* 106:1392-1399 (2005); Davis et al., "Constitutive Nuclear Factor κB Activity is Required for Survival of Activated B Cell-like Diffuse Large B Cell Lymphoma Cells," *J Exp Med* 194:1861-1874 (2001)), and that small molecules that inhibit IκB kinases (IKK) are selectively toxic for these two DLBCL subgroup cells (Lam et al., "Small Molecule Inhibitors of IκB Kinase Are Selectively Toxic for Subgroups of Diffuse Large B-cell Lymphoma Defined by Gene Expression Profiling," *Clin Cancer Res* 11:28-40 (2005)). These studies highlight the NF-κB pathway as a promising therapeutic target in B-lymphomas that depend on NF-κB activity for proliferation and survival.

Multiple myeloma ("MM") is a B cell malignancy characterized by the latent accumulation in bone marrow of secretory plasma cells with a low proliferative index and an extended life span. The disease ultimately attacks bones and bone marrow, resulting in multiple tumors and lesions throughout the skeletal system. Approximately 1% of all cancers, and slightly more than 10% of all hematologic malignancies, can be attributed to multiple myeloma. Incidence of MM increases in the aging population, with the median age at time of diagnosis being about 61 years. Current treatment protocols, which include a combination of chemotherapeutic agents such as vincristine, β-chloro-nitrosourea (BCNU), melphalan, cyclophosphamide, Adriamycin, and prednisone or dexamethasone, yield a complete remission rate of only about 5%, and median survival is approximately 36-48 months from the time of diagnosis. Recent advances using high dose chemotherapy followed by autologous bone marrow or peripheral blood progenitor cell (PBMC) transplantation have increased the complete remission rate and remission duration. Yet overall survival has only been slightly prolonged, and no evidence for a cure has been obtained. Ultimately, all MM patients relapse, even under maintenance therapy with interferon-α (IFN-α) alone or in combination with steroids.

MM has been previously associated with enhanced NF-κB activity (Berenson et al., "The Role of Nuclear Factor-κB in the Biology and Treatment of Multiple Myeloma," *Semin. Oncol.* 28(6):626-33 (2001). New evidence on the molecular mechanisms that underlie aberrant NF-κB activity in MM tumor cells has been found recently (Annunziata et al., "Frequent Engagement of the Classical and Alternative NF-κB Pathways by Diverse Genetic Abnormalities in Multiple Myeloma," *Cancer Cell* 12(2):115-30 (2007); Keats et al., "Promiscuous Mutations Activate the Noncanonical NF-κB Pathway in Multiple Myeloma," *Cancer Cell* 12(2):131-44 (2007)). The results reported in these studies confirm that diverse mutations can lead to pathological activation of NF-κB signaling in MM, and result in a shift of plasma cells from dependence on the microenvironment to an environment-independent state during progression of MM.

The NF-κB family consists of five members in mammals: p65 (RelA), RelB, c-Rel, NF-κB1(p105/p50), and NF-κB2 (p100/p52). Members of NF-κB proteins form homo- or heterodimers and are retained in the cytoplasm prior to activation by the associated IκB proteins, or the precursor proteins p100 or p105, which contain the ankyrin repeats present also in the IκB proteins and, thus, can also function as IκB proteins. Extracellular signals induce NF-κB activation through two major pathways: the classical (also called the canonical pathway) and the alternative (the non-canonical) pathways. Activation of these pathways leads to activation of IKK and degradation or processing of IκB proteins, resulting in the release of sequestered NF-κB proteins and their subsequent translocation into the nucleus and target gene activation (Hayden et al., "Signaling to NF-κB," *Genes Dev* 18:2195-2224 (2004); Karin, "NF-κB and Cancer: Mechanisms and Targets," *Mol Carcinog* 45:355-361 (2006); Scheidereit, "IκB Kinase Complexes: Gateways to NF-κB Activation and Transcription," *Oncogene* 25:6685-6705 (2006)). Abnormal activation of NF-κB contributes to tumor development and progression, as well as to the resistance of cancer cells to chemotherapeutic agents and radiation therapy (Kim et al., "NF-κB and IKK as Therapeutic Targets in Cancer," *Cell Death Differ* 13(5):738-47 (2006); Karin, "Nuclear Factor-κB in Cancer Development and Progression," *Nature* 441:431-436 (2006)). Thus, inhibition of NF-κB activation represents a promising approach for cancer therapy (Karin et al., "The IKK NF-κB System: A Treasure Trove for Drug Development," *Nat Rev Drug Discov* 3:17-26 (2004)). However, as NF-κB is expressed ubiquitously and is involved in a wide variety of normal cellular functions, a general inhibition of NF-κB activity would likely cause serious side effects (Kim et al., "NF-κB and IKK as Therapeutic Targets in Cancer," *Cell Death Differ* 13(5):738-47 (2006); Luo et al., "IKK/NF-κB Signaling: Balancing Life and Death—A New Approach to Cancer Therapy," *J Clin Invest* 115:2625-2632 (2005); Li et al., "Inflammation-associated Cancer: NF-κB is the Lynchpin," *Trends Immunol* 26:318-325 (2005)). To achieve the specificity required for effective therapeutic intervention, it may be necessary to target cancer cell- or signal-specific regulators of NF-κB activation pathways.

The B cell-activating factor belonging to the tumor necrosis factor family (BAFF, also known as BlyS, TALL-1, THANK, zTNF-4, CD257 and TNFSF-13B) is critical for the development and survival of normal B lymphocytes, and activates NF-κB through both the classical and the alternative activation pathways in B cells (Kayagaki et al., "BAFF/BLyS Receptor 3 Binds the B Cell Survival Factor BAFF Ligand Through a Discrete Surface Loop and Promotes Processing of NF-κB2," *Immunity* 17:515-524 (2002); Claudio et al., "BAFF-induced NEMO-independent Processing of NF-κB2 in Maturing B cells," *Nat Immunol* 3:958-965 (2002); Schneider, P., "The Role of APRIL and BAFF in Lymphocyte Activation," *Curr Opin Immunol* 17:282-289 (2005); Sutherland et al., "Targeting BAFF: Immunomodulation for Autoimmune Diseases and Lymphomas," *Pharmacol Ther* 112:774-786 (2006); Hatada et al., "NF-κB1 p50 is Required for BLyS Attenuation of Apoptosis but Dispensable for Processing of NF-κB2 p100 to p52 in Quiescent Mature B Cells," *J Immunol* 171:761-768 (2003)). Dysregulated BAFF signaling has been associated with various B-cell malignancies. Elevated levels of BAFF have been detected in the serum of patients with various types of B-cell malignancies, and malignant B cells from patients express abnormally high levels of BAFF and one or more BAFF receptors (He et al., "Lymphoma B Cells Evade Apoptosis Through the TNF Family Members BAFF/BLyS and APRIL," *J Immunol* 172:3268-3279 (2004); Novak et al., "Expression of BLyS and its Receptors in B-cell non-Hodgkin Lymphoma: Correlation with Disease Activity and Patient Outcome," *Blood* 104:2247-2253 (2004); Novak et al., "Aberrant Expression of B-lymphocyte Stimulator by B Chronic Lymphocytic Leukemia Cells: A Mechanism for Survival," *Blood* 100:2973-2979 (2002); Briones et al., "BLyS and BLyS Receptor Expression in non-Hodgkin's Lymphoma," *Exp Hematol* 30:135-141 (2002); Fu et al., "Constitutive NF-κB and NFAT Activation Leads to Stimulation of the BLyS Survival Pathway in Aggressive B Cell Lymphomas," *Blood* 107(11):4540-4548 (2006); Moreaux et al., "BAFF and APRIL Protect Myeloma Cells from Apoptosis Induced by Interleukin 6 Deprivation and Dexamethasone," *Blood* 103:3148-3157 (2004); Elsawa et al., "B-lymphocyte stimulator (BLyS) Stimulates Immunoglobulin Production and Malignant B-cell Growth in Waldenstrom's Macroglobulinemia," *Blood* 107(7):2882-2888 (2006); Kern et al., "Involvement of BAFF and APRIL in the Resistance to Apoptosis of B-CLL Through an Autocrine Pathway," *Blood* 103:679-688 (2004). It has been shown that BAFF functions as a crucial autocrine and paracrine survival factor for malignant B cells (Sutherland et al., "Targeting BAFF: Immunomodulation for Autoimmune Diseases and Lymphomas," *Pharmacol Ther* 112:774-786 (2006); He et al., "Lymphoma B Cells Evade Apoptosis Through the TNF Family Members BAFF/BLyS and APRIL," *J Immunol* 172:3268-3279 (2004); Novak et al., "Aberrant Expression of B-lymphocyte Stimulator by B Chronic Lymphocytic Leukemia Cells: A Mechanism for Survival," *Blood* 100:2973-2979 (2002); Fu et al., "Constitutive NF-κB and NFAT Activation Leads to Stimulation of the BLyS Survival Pathway in Aggressive B Cell Lymphomas *Blood* 107(11):4540-4548 (2006); Moreaux et al., "BAFF and APRIL Protect Myeloma Cells from Apoptosis Induced by Interleukin 6 Deprivation and Dexamethasone," *Blood* 103:3148-3157 (2004); Novak et al., "Expression of BCMA, TACI, and BAFF-R in Multiple Myeloma: A Mechanism for Growth and Survival," *Blood* 103:689-694 (2004); Elsawa et al., "B-lymphocyte Stimulator (BLyS) Stimulates Immunoglobulin Production and Malignant B-cell Growth in Waldenstrom's Macroglobulinemia," *Blood* 107(7):2882-2888 (2006); Kern et al., "Involvement of BAFF and APRIL in the Resistance to Apoptosis of B-CLL Through an Autocrine Pathway," *Blood* 103:679-688 (2004); Endo et al., "BAFF and APRIL Support Chronic Lymphocytic Leukemia B-cell Survival Through Activation of the Canonical NF-κB pathway," *Blood* 109:703-710 (2007); Nishio et al., "Nurselike Cells Express BAFF and APRIL, Which Can Promote Survival of Chronic Lymphocytic Leukemia Cells Via a Paracrine Pathway Distinct from That of SDF-1α," *Blood* 106:1012-1020 (2005), making the BAFF signaling pathway an attractive therapeutic target for B-cell malignancies. Despite the importance of BAFF signaling in both normal and malignant B cells, the mechanisms by which BAFF activates downstream events, including NF-κB activation, remain to be elucidated.

Protein kinase C-associated kinase PKK (also known as DIK and RIP4) was initially identified as a protein kinase C β- and δ-interacting protein (Bahr et al., "DIK, a Novel Protein Kinase that Interacts with Protein Kinase Cdelta. Cloning, Characterization, and Gene Analysis," *J Biol Chem* 36350-36357 (2000); Chen et al., "Protein Kinase C-associated Kinase (PKK), a Novel Membrane-associated, Ankyrin Repeat-containing Protein Kinase," *J Biol Chem* 276:21737-21744 (2001)). It belongs to the RIP kinase family, and shares high sequence homology at the N-terminal kinase domain with other members of this kinase family but contains unique C-terminal ankryin repeats (Meylan et al., "The RIP Kinases: Crucial Integrators of Cellular Stress," *Trends Biochem Sci* 30:151-159 (2005)). Mice deficient in PKK die soon after birth, likely due to suffocation caused by abnormal epidermal differentiation (Holland et al., "RIP4 is an Ankyrin Repeat-containing Kinase Essential for Keratinocyte Differentiation," *Curr Biol* 12:1424-1428 (2002)). It has been shown that PKK activates NF-κB when overexpressed in non-lymphoid cells (Moran et al., "Protein Kinase C-associated Kinase can Activate NFκB in Both a Kinase-dependent and a Kinase-independent Manner," *J Biol Chem* 278:21526-21533 (2003); Meylan et al., "RIP4 (DIK/PKK), a Novel Member of the RIP Kinase Family, Activates NF-κB and is Processed During Apoptosis," *EMBO Rep* 3:1201-1208 (2002); Muto et al., "Protein Kinase C-associated Kinase (PKK) Mediates Bcl10-independent NF-κB Activation Induced by Phorbol Ester," *J Biol Chem* 277:31871-31876 (2002)).

Despite these prior reports on the relationship between PKK and NF-κB activation, these prior reports fail to demonstrate any function of PKK in the proliferation/survival of cancer cells, particularly B cell malignancies such as lymphomas and multiple myeloma.

The present invention is directed to overcoming these and other deficiencies in the art.

SUMMARY OF THE INVENTION

A first aspect of the present invention relates to a method of treating a B-cell malignancy that includes administering to a patient an amount of an inhibitor of protein kinase C-associated kinase (PKK) activity that is effective to cause cell death of a malignant B cell, thereby treating the B-cell malignancy. In particular, the treatment of B cell lymphomas and multiple myeloma is contemplated.

A second aspect of the present invention relates to a method of causing cell death of a malignant B cell that includes: introducing an inhibitor of protein kinase C-associated kinase (PKK) activity into a malignant B cell under conditions effective to cause cell death of the malignant B cell.

A third aspect of the present invention relates to a pharmaceutical composition that includes an inhibitor of PKK activity. This aspect of the present invention also encompasses combination therapies that include the inhibitor of PKK activity in combination with a chemotherapeutic agent, radiation therapy, immunotherapy agents, or combinations thereof. According to one embodiment, the pharmaceutical composition includes a drug delivery vehicle that targets a malignant B cell. Therapeutic systems for such combination therapy are also encompassed.

A fourth aspect of the present invention relates to an inhibitory nucleic acid molecule that inhibits the expression of or activity of PKK.

A fifth aspect of the present invention relates to an expression vector encoding an inhibitory nucleic acid molecule of the present invention.

The present invention demonstrates the requirement for PKK in NF-κB activation and survival in B cell malignancies such as lymphomas and multiple myeloma. It was found that PKK regulates NF-κB activation in lymphomatic B cells and myeloma plasma cells, and B cell activation factor ("BAFF") was identified as one of the upstream signaling molecules that requires PKK for NF-κB activation in many of these cells. Inhibition of PKK expression impairs survival of B cell lymphomas and multiple myeloma plasma cells in vitro, and in vivo tumor growth of implanted B cell tumors. The present invention provides additional evidence to support the use of inhibitors of PKK activity or expression in combination with chemotherapeutic agents for the treatment of various B cell malignancies, including lymphomas and multiple myeloma.

BRIEF DESCRIPTION OF THE DRAWINGS

FIGS. 1A-F show that PKK regulates NF-κB activity in DLBCL cells. FIG. 1A shows that overexpression of PKK activates NF-κB in DLBCL cells. SUDHL-6 cells stably carrying pMIG vector or expressing Flag-tagged PKK-N were cultured in serum-free medium for 20 hours. The expression of the indicated proteins involved in NF-κB signaling was analyzed by western blotting. p-IκBα, p-IKKα, p-IKKβ represent phosphorylated forms of IκBα, IKKα and IKKβ, respectively. Analysis of γ-tubulin was used as the equal loading control. FIG. 1B shows that suppression of PKK expression inhibits NF-κB activity in ABC DLBCL cells. OCI-Ly10 cells were infected with lentiviruses expressing either a control shRNA (L-shControl) or a PKK-specific shRNA (L-shPKK-1). Three days post-infection, RNA levels of PKK in the indicated cells were analyzed by RT-PCR (left panels), and expression of the indicated proteins was analyzed by western blotting (right panels). Analysis of GAPDH and γ-tubulin was used as loading controls. FIG. 1C shows that PKK knockdown leads to inhibition of NF-κB DNA-binding activity. OCI-Ly10 cells were infected with lentiviruses expressing a control shRNA (L-shControl) or a PKK-specific shRNA (shPKK-1 or shPKK-1). Sixty-four hours post-infection, nuclear extracts were prepared and the DNA-binding activity of the indicated NF-κB subunit was analyzed by an ELISA-based assay (TransAM NF-κB family transcription factor assay kit (Active Motif). The assays were carried out in triplicates. shControl-expressing cells contain significantly higher NF-κB DNA-binding activity than cells expressing an shPKK (P<0.01 for all NF-κB subunits, except for RelB subunit). FIG. 1D shows that suppression of PKK expression results in decreased NF-κB activity in GCB DLBCL cell line SUDHL-6 cells. SUDHL-6 cells stably expressing either the control shRNA (shControl) or a PKK-specific shRNA (shPKK-1 or shPKK-2) were cultured in serum-free medium overnight. The levels of PKK RNA in the indicated cells were analyzed by RT-PCR (left panels), and the expression of the indicated proteins was analyzed on western blots (right panels). FIG. 1E shows that suppression of PKK inhibits NF-κB activity in GCB DLBCL cell line OCI-Ly7 cells. OCI-Ly7 cells stably expressing either shControl or shPKK-1 were cultured in serum-free medium overnight. Expression of PKK RNA (left panels) and the indicated proteins involved in NF-κB signaling (right panels) were analyzed as described in FIG. 1D. FIG. 1F shows that PKK knockdown reduces NF-κB DNA-binding activity in GCB DLBCL cells. SUDHL-6 cells stably expressing the indicated shRNA were cultured in serum-free medium overnight. Nuclear extracts were prepared and the DNA-binding activity of p65 and p50 were assayed as described for FIG. 1C. The difference between control cells and cells expressing an shPKK in NF-κB DNA-binding activity is statistically significant (P<0.01).

FIG. 2A shows the surface expression of the indicated BAFF receptors in SUDHL-6 cells. SUDHL-6 cells were incubated with antibodies specific for hBR3, hBCMA or hTACI (filled histograms) or a control antibody (open histograms). After incubating with secondary antibodies, the expression of the indicated BAFF receptors was analyzed by flow cytometry (Endo et al., "BAFF and APRIL Support Chronic Lymphocytic Leukemia B-cell Survival through Activation of the Canonical NF-κB pathway," *Blood* 109:703-710 (2007), which is hereby incorporated by reference in its entirety). FIG. 2B shows that suppression of PKK expression inhibits NF-κB activation induced by BAFF. SUDHL-6 cells stably expressing shControl, shPKK-1 or shPKK-2 were treated with BAFF (200 ng/ml) for 15 minutes in serum-free medium. The expression levels of the indicated proteins were analyzed on western blots. FIG. 2C shows that PKK knockdown leads to inhibition of nuclear translocation of NF-κB proteins. SUDHL-6 cells stably expressing the indicated shRNA were treated with BAFF (500 ng/ml) for 6 hours in serum-free-medium. Nuclear fractions were prepared according to the instructions by the manufacturer (Active Motif), and the levels of the indicated NF-κB subunits in each fraction were analyzed by western blotting. FIG. 2D shows that suppression of PKK expression inhibits BAFF-induced NF-κB DNA-binding activity. SUDHL-6 cells expressing the indicated shRNA were treated as described in FIG. 2C, and the DNA-binding activity of the indicted NF-κB subunit was assayed as described in FIG. 1C. The difference between control cells and cells expressing an shPKK in DNA-binding activity for all tested NF-κB subunits is significance ($P<0.01$). FIG. 2E shows that SUDHL-6 cells expressing either shControl or shPKK-1 that were treated with BAFF for the indicated time. IKK (I κB kinase) complex was immunoprecipitated with an IKKβ specific antibody. The kinase activity of the immunoprecipitated IKK complex was assayed in vitro using GST-IκBα (amino acids 1-54) as a substrate (upper panel). The amounts of IKKβ protein in the immunoprecipitated samples were analyzed by western blotting using an IKKβ antibody (lower panel).

FIGS. 3A-B show that suppression of PKK expression inhibits NF-κB activation induced by BAFF. FIG. 3A shows SUDHL-6 cells stably expressing shControl, shPKK-1 or shPKK-3 that were cultured in serum-free medium overnight and then treated with BAFF (200 ng/ml) for 5 minutes. The expression levels of the indicated proteins were analyzed on western blots. FIG. 3B shows OCI-Ly7 cells stably expressing shControl or shPKK-1 that were cultured in serum-free medium overnight and then treated with BAFF for 30 minutes. The expression of the indicated proteins was analyzed by western blotting.

FIGS. 4A-C show that suppression of PKK expression results in cell death of OCI-Ly10 cells. FIG. 4A shows OCI-Ly10 cells that were infected with lentiviruses expressing either L-shControl or L-shPKK-1, together with the GFP. At the indicated times after infection, the GFP-positive fractions were analyzed by flow cytometry. The GFP-positive fractions were normalized to the samples harvested at 2 days post-infection. Means and standard deviations from 3 separate experiments are depicted. FIG. 4B shows OCI-Ly10 cells that were infected as described in FIG. 4A, and the cell death was analyzed at two and four days post-infection, respectively, using the Annexin V-PE apoptosis detection kit (BD Bioscience). The results shown are averaged from two separate experiments. FIG. 4C shows protein expression levels (for indicated proteins) in OCI-Ly10 cells infected as described with respect to FIG. 4A. Three days post-infection, expression of the indicated proteins was analyzed on western blots.

FIG. 5A shows OCI-Ly10 cells that were infected with lentiviruses expressing either L-shControl or L-shPKK-2. At the indicated times after infection, the GFP-positive fractions were analyzed by flow cytometry. The GFP-positive fractions were normalized to the samples harvested at 2 days post-infection. FIG. 5B shows OCI-Ly3 cells that were infected with the lentiviruses expressing either L-shControl or L-shPKK-1. At the indicated times after infection, the GFP-positive fractions were analyzed by flow cytometry. The GFP-positive fractions were normalized to the samples harvested at 4 days post-infection.

FIGS. 6A-D show the effect of PKK knockdown on survival of SUDHL-6 cells. FIG. 6A shows SUDHL-6 cells stably expressing shControl or shPKK-1 that were cultured in the medium containing 10% serum. The live cells were measured by the 3-[4,5-dimethylthiazol-2-yl]-2,5-diphenyl tetrazolium bromide (MTT) assay. The results were normalized to the absorbance readings at the time the cells were plated (0 hr). Mean results and deviations from three experiments are shown. FIG. 6B shows SUDHL-6 cells stably expressing shControl or shPKK-1 that were cultured in the medium containing the indicated concentrations of serum. The relative numbers of live cells were analyzed at the indicated times as described with respect to FIG. 6A. FIG. 6C shows SUDHL-6 cells stably expressing shControl or sh-PKK-1 that were cultured in the medium containing 0 or 10% serum for 24 hours. The annexin V-positive cells (dying or dead) cells were analyzed as described in the accompanying Examples. The data represent the mean results of three independent experiments. FIG. 6D shows the extent of protein cleavage for the indicated proteins in the shRNA-expressing SUDHL-6 cells that were cultured in medium containing 0 or 10% serum for 24 hours. The cleavage of PARP (poly(ADP-ribose)polymerase) and caspase 3 was analyzed on western blots. The analysis of IKKα was used as the equal loading control.

FIG. 10A shows SUDHL-6 cells expressing shControl or shPKK-1 that were treated with etoposide at the indicted concentrations for thirty-six hours. The relative number of live cells were analyzed by MTT assay. The absorbance readings from the cells treated with the vehicle (DMSO) were set at 100%. The mean results and standard deviations from three separate experiments are depicted. FIG. 10B shows SUDHL-6 cells expressing shControl or a shPKK that were treated with CHOP for 72 hours. The relative numbers of live cells were analyzed as described with respect to FIG. 6A. 1×CHOP contains cyclophosphamide monophosphate, doxorubicin, vincristine and prednisone at concentrations of 5.84 pM, 1.5 pM, 260 pM and 1.0 µM, respectively (Mohammad et al., "Genistein Sensitizes Diffuse Large Cell Lymphoma to CHOP (cyclophosphamide, doxorubicin, vincristine, prednisone) Chemotherapy," *Mol Cancer Ther* 2:1361-1368 (2003), which is hereby incorporated by reference in its entirety).

DETAILED DESCRIPTION OF THE INVENTION

Figure 2A:
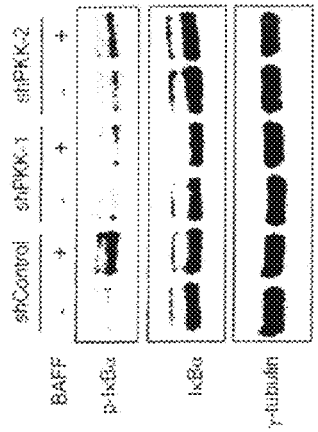
FIGS. 2A-E show that PKK regulates NF-κB activation induced by BAFF.
Figure 2B:
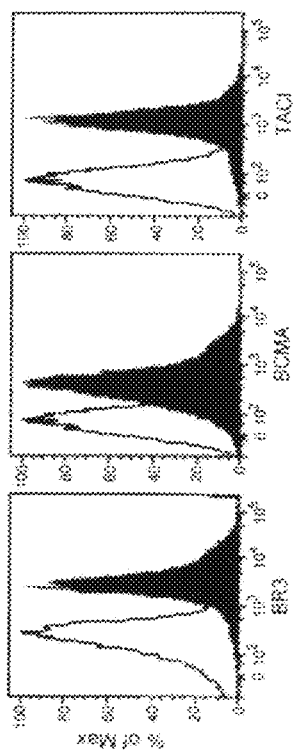
Figure 2C:
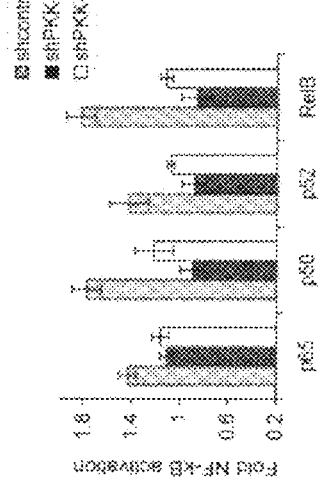
Figure 2D:
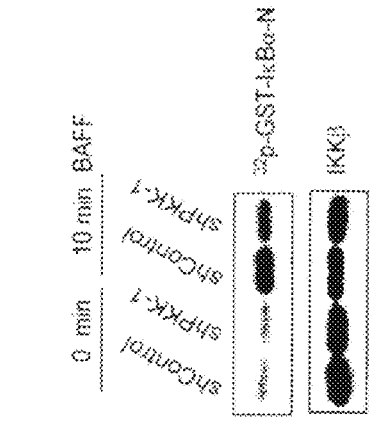

The present invention demonstrates that protein kinase C-associated kinase (PKK) regulates NF-κB activation in B cell malignancies, including lymphomas and multiple myeloma, and further demonstrates that inhibition of PKK activity or expression impairs survival of malignant B cells both in vitro and in vivo, and sensitizes malignant B cells to treatment with chemotherapeutic agents.

According to one aspect, the present invention relates to a method of causing cell death of malignant B-cells that includes introducing an inhibitor of PKK activity into a malignant B cell under conditions effective to cause cell death of the malignant B cell.

According to a related aspect, the present invention also relates to a method of treating B cell malignancies that includes administering to a patient an amount of an inhibitor of PKK activity that is effective to cause cell death of a B cell malignancy, thereby treating the B cell malignancy. As used herein, the treatment of a B cell malignancy is intended to encompass a reduction in the rate of proliferation of malignant B cells, thereby improving quality of life and lifespan following diagnosis, as well as the complete destruction of tumor cells, which may result in remission of the B cell malignancy.

The patient can be any mammalian patient that suffers from a B cell malignancy. Preferably, the patient is a human or non-human primate, a dog, a cat, a horse, a cow, a goat, a sheep, a rabbit, or a rodent (e.g., mouse or rat).

It is believed that B cell malignancies require PKK activity for continued survival via anti-apoptotic activity of NF-κB. As demonstrated in the examples, this is true for several different B cell lymphoma cell lines from several mammals and induced in vivo tumors, as well as multiple myeloma cell lines. Thus, as used herein, the term "B cell malignancy" is intended to apply to any cancerous B cell condition, such as multiple myeloma (plasma cells) or various lymphomas, but preferably those B cell malignancies that require PKK activity for continued survival. Exemplary B cell lymphomas that can be treated in accordance with the present invention include, without limitation, both Hodgkin's and Non-Hodgkin's lymphomas, such as small lymphocytic lymphomas, follicular lymphomas, large cell lymphomas (e.g., diffuse large cell lymphomas (DLBCL) and diffuse mixed cell lymphomas), small non-cleaved cell lymphomas, diffuse small cell or Mantle cell lymphomas, Burkitt's lymphoma, Burkitt-like lymphoma, lymphoplasmocytic lymphoma, marginal zone lymphomas, precursor B-lymphoblastic lymphomas, etc. Various multiple myeloma types, including IgG myeloma, IgA myeloma, IgD myeloma, IgE myeloma, and light chain (κ or λ) myelomas, can be treated in accordance with the present invention. The malignant B cells to be destroyed in accordance with the present invention can be in vitro (ex vivo) or in vivo.

The inhibitor of PKK activity can act directly on PKK (e.g., an inhibitor of PKK) or act to reduce or eliminate the expression level of PKK in targeted B cell lymphomas or myeloma plasma cells.

Exemplary direct inhibitors of PKK activity include, without limitation, antibodies or antibody fragments that bind specifically to PKK, anti-PKK nucleic acid aptamers, C-terminal fragments of PKK that can act as dominant negative regulators of NF-κB activity, and small molecule PKK inhibitors.

Anti-PKK antibodies can be polyclonal antibodies or monoclonal antibodies, although monoclonal antibodies are preferred because of their specificity. The antibody can also be a polyclonal preparation rendered monospecific.

Various methods of producing antibodies with a known antigen are well-known to those ordinarily skilled in the art (ANTIBODIES: A LABORATORY MANUAL (Harlow & Lane eds., 1988), which is hereby incorporated by reference in its entirety). In particular, suitable antibodies may be produced by chemical synthesis, by intracellular immunization (i.e., intrabody technology), or preferably, by recombinant expression techniques. Methods of producing antibodies may further include the hybridoma technology well-known in the art.

In particular, monoclonal antibody production may be effected by techniques which are well-known in the art. Basically, the process involves first obtaining immune cells (lymphocytes) from the spleen of a mammal (e.g., mouse) which has been previously immunized with the antigen of interest either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler & Milstein, "Continuous Cultures of Fused Cells Secreting Antibody of Predefined Specificity," *Nature*, 256:495-497 (1975), which is hereby incorporated by reference in its entirety.

Mammalian lymphocytes are immunized by in vivo immunization of the animal (e.g., a mouse) with the protein or polypeptide of interest (i.e., PKK or suitable fragments thereof that contain the kinase domain). Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents (see Milstein & Kohler, "Derivation of Antibody-producing Tissue Culture and Tumor Lines by Cell Fusion," Eur. J. Immunol. 6:511-519 (1976), which is hereby incorporated by reference in its entirety). This immortal cell line, which is preferably murine, but may also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also well known. Typically, such antibodies can be raised by administering the protein or polypeptide of interest (i.e., PKK or suitable fragments thereof) subcutaneously to New Zealand white rabbits which have first been bled to obtain pre-immune serum. The antigens can be injected at a total volume of 100 µl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthanized with pentobarbital 150 mg/Kg IV. This and other procedures for raising polyclonal antibodies are disclosed in ANTIBODIES: A LABORATORY MANUAL (Harlow & Lane eds., 1988), which is hereby incorporated by reference in its entirety.

In addition to utilizing whole antibodies, the methods of the present invention encompass use of binding portions of such antibodies. Such binding portions include Fab fragments, F(ab)$_2$ fragments, Fab' fragments, F(ab')$_2$ fragments, Fd fragments, Fd' fragments, Fv fragments, and minibodies, e.g., 61-residue subdomains of the antibody heavy-chain variable domain (Pessi et al., "A Designed Metal-binding Protein with a Novel Fold," Nature 362:367-369 (1993), which is hereby incorporated by reference in its entirety). Domain antibodies (dAbs) are also suitable for the methods of the present inventions (Holt et al., "Domain Antibodies: Proteins for Therapy," Trends Biotechnol. 21:484-90 (2003), which is hereby incorporated by reference in its entirety). These antibody fragments can be made by conventional procedures, such as proteolytic fragmentation procedures, as described in J. Goding, MONOCLONAL ANTIBODIES: PRINCIPLES AND PRACTICE 98-118 (1984), which is hereby incorporated by reference in its entirety.

The antibodies may be from humans, or from animals other than humans, preferably mammals, such as rat, mouse, guinea pig, rabbit, goat, sheep, and pig, or avian species such as chicken. Preferred are mouse monoclonal antibodies and antigen-binding fragments or portions thereof. In addition, chimeric antibodies and hybrid antibodies are embraced by the present invention. Techniques for the production of chimeric antibodies are described in, e.g., Morrison et al., "Chimeric Human Antibody Molecules: Mouse Antigen-binding Domains with Human Constant Region Domains," Proc. Nat'l Acad. Sci. USA 81:6851-5 (1984), Neuberger et al., "Recombinant Antibodies Possessing Novel Effector Functions," Nature 312:604-8 (1984), and Takeda et al., "Construction of Chimaeric Processed Immunoglobulin Genes Containing Mouse Variable and Human Constant Region Sequences," Nature 314:452-4 (1985), each of which is hereby incorporated by reference in its entirety. For human therapeutic purposes, humanized antibodies or fragments are preferred.

Further, single chain antibodies are also suitable for the present invention (e.g., U.S. Pat. Nos. 5,476,786 to Huston and 5,132,405 to Huston & Oppermann; Huston et al., "Protein Engineering of Antibody Binding Sites: Recovery of Specific Activity in an Anti-digoxin Single-chain Fv Analogue Produced in Escherichia coli," Proc. Nat'l Acad. Sci. USA 85:5879-83 (1988); U.S. Pat. No. 4,946,778 to Ladner et al.; Bird et al., "Single-chain Antigen-binding Proteins," Science 242:423-6 (1988); Ward et al., "Binding Activities of a Repertoire of Single Immunoglobulin Variable Domains Secreted from Escherichia coli," Nature 341:544-6 (1989), each of which is hereby incorporated by reference in its entirety). Single chain antibodies are formed by linking the heavy and light immunoglobulin chain fragments of the Fv region via an amino acid bridge, resulting in a single chain polypeptide. Univalent antibodies are also embraced by the present invention.

Exemplary antibodies include, without limitation, RIP4 monoclonal antibodies 2G3 and 1G2 available from Abnova.

A number of antibody mimics are known in the art including, without limitation, those known as monobodies, which are derived from the tenth human fibronectin type III domain ($^{10}$Fn3) (Koide et al., "The Fibronectin Type III Domain as a Scaffold for Novel Binding Proteins," J. Mol. Biol. 284:1141-1151 (1998); Koide et al., "Probing Protein Conformational Changes in Living Cells by Using Designer Binding Proteins: Application to the Estrogen Receptor," Proc. Natl Acad. Sci. USA 99:1253-1258 (2002), each of which is hereby incorporated by reference in its entirety); and those known as affibodies, which are derived from the stable α-helical bacterial receptor domain Z of staphylococcal protein A (Nord et al., "Binding Proteins Selected from Combinatorial Libraries of an α-helical Bacterial Receptor Domain," Nature Biotechnol. 15(8):772-777 (1997), which is hereby incorporated by reference in its entirety). Variations in these antibody mimics can be created by substituting one or more domains of these polypeptides and then screening the modified monobodies or affibodies for CYLD binding and inhibitory activity.

Anti-PKK nucleic acid aptamers can be formed of DNA or RNA, and are characterized by specificity for PKK domains required for activation of PKC subtypes or NF-κB. Aptamers are single-stranded, partially single-stranded, partially double-stranded, or double-stranded nucleotide sequences, advantageously a replicatable nucleotide sequence, capable of specifically recognizing a selected non-oligonucleotide molecule or group of molecules by a mechanism other than Watson-Crick base pairing or triplex formation. Aptamers include, without limitation, defined sequence segments and sequences comprising nucleotides, ribonucleotides, deoxyribonucleotides, nucleotide analogs, modified nucleotides and nucleotides comprising backbone modifications, branchpoints and nonnucleotide residues, groups or bridges.

Nucleic acid aptamers include multivalent aptamers and bivalent aptamers. Methods of making bivalent and multivalent aptamers and their expression in multi-cellular organisms are described in U.S. Pat. No. 6,458,559 to Shi et al., which is hereby incorporated by reference in its entirety. A method for modular design and construction of multivalent nucleic acid aptamers, their expression, and methods of use are described in U.S. Patent Publication No. 2005/0282190 to Shi et al, which is hereby incorporated by reference in its entirety.

Aptamers may be designed to inhibit the activity of PKK in activating PKC subtypes or NF-κB as it relates to promoting cell survival, particularly anti-apoptotic survival of malignant B cells (e.g., lymphomas and myeloma plasma cells).

Identifying suitable nucleic acid aptamers that inhibit the activity of PKK, as described above, basically involves selecting aptamers that bind PKK mRNA with sufficiently high affinity (e.g., $K_d$=20-50 nM) and specificity from a pool of nucleic acids containing a random region of varying or predetermined length (Shi et al., "A Specific RNA Hairpin Loop Structure Binds the RNA Recognition Motifs of the Drosophila SR Protein B52," Mol. Cell Biol. 17:1649-1657 (1997); Shi, "Perturbing Protein Function with RNA Aptamers" (thesis, Cornell University) microformed on (University Microfilms, Inc. 1997), each of which is hereby incorporated by reference in their entirety).

For example, identifying suitable nucleic acid aptamers can be carried out using an established in vitro selection and amplification scheme known as SELEX. The SELEX scheme is described in detail in U.S. Pat. No. 5,270,163 to Gold et al.; Ellington and Szostak, "In Vitro Selection of RNA Molecules that Bind Specific Ligands," Nature 346:818-822 (1990); and Tuerk & Gold, "Systematic Evolution of Ligands by Exponential Enrichment: RNA Ligands to Bacteriophage T4 DNA Polymerase," Science 249:505-510 (1990), each of which is hereby incorporated by reference in its entirety. The SELEX procedure can be modified so that an entire pool of aptamers with binding affinity can be identified by selectively partitioning the pool of aptamers. This procedure is described in U.S. Patent Application Publication No. 2004/0053310 to Shi et al., which is hereby incorporated by reference in its entirety.

Once selected for their binding affinity, aptamers that bind to and inhibit activity of PKK can be identified using the screening procedures described in the following paragraph.

Small molecule inhibitors of PKK activity can be screened using any of a variety of screening methods, including library screening methods. Basically, compounds to be screened can be exposed to PKK and the ability of PKK to activate NF-κB can be assessed. A large number of screening assays are described in greater detail in U.S. Patent Application Publ. No. 20030199462 to Nunez et al., which is hereby incorporated by reference in its entirety.

Another class of inhibitors relates to PKK C-terminal fragments that act as dominant negative regulators of NF-κB activity (i.e., the presence of these PKK fragments inhibits NF-κB activity). An exemplary PKK C-terminal fragment lacking the kinase domain is identified in Meylan et al., "RIP4 (DIK/PKK), a Novel, Member of the RIP Kinase Family, Activates NF-κB and Is Processed During Apoptosis," EMBO Reports 3(12):1201-1208 (2002), which is hereby incorporated by reference in its entirety.

Dominant negative PKK fragments lacking the kinase domain can be prepared using knowledge of the primary nucleotide and protein sequence (see Genbank accession numbers AJ278016 (human) and AF302127 (mouse), each of which is hereby incorporated by reference in its entirety). Basically, this involves preparing a nucleic acid molecule that encodes the polypeptide of interest, and then inserting the nucleic acid molecule into an expression vector that contains all required regulatory elements to induce expression of the polypeptide once the expression vector is taken up inside recombinant host cells (e.g., bacteria, plant cells, yeast, protozoa, mammalian cells, etc.) The recombinant nucleic acid molecule can be stably expressed or transiently expressed. Regardless, the expressed polypeptide can be recovered or isolated from the recombinant host cells using traditional protein recovery techniques. The expressed polypeptide can also be purified (e.g., at least 95% pure, or more preferably 98% pure) using standard purification procedures including chromatography procedures and epitope-based purification. See JOSEPH SAMBROOK & DAVID W. RUSSELL, MOLECULAR CLONING: A LABORATORY MANNUAL (3d ed. 2001); SHORT PROTOCOLS IN MOLECULAR BIOLOGY (Frederick M. Ausubel et al. eds., 1999); U.S. Pat. No. 4,237,224 to Cohen and Boyer, each of which is hereby incorporated by reference in their entirety).

The inhibitors of PKK activity that act to reduce or eliminate the expression of PKK in targeted B lymphoma or myeloma cells are inhibitor nucleic acid molecules. Typically, the inhibitory nucleic acid molecule is the product of an expression vector, which upon being taken up into the targeted B cells expresses the inhibitory nucleic acid molecule to reduce or eliminate PKK expression. Alternatively, the inhibitory nucleic acid molecule can be administered directly as a component of a pharmaceutical product, and upon cell uptake it can reduce or eliminate PKK expression.

The term "inhibitory nucleic acid molecule," as used herein, is intended to encompass any nucleic acid molecule that interferes with or inhibits expression of a target gene or genomic sequence, typically though not exclusively by RNA interference (RNAi). Such inhibitory nucleic acid molecules include, but are not limited to, RNA molecules that are homologous to the target gene or genomic sequence, or a fragment thereof, short interfering RNA (siRNA), short hairpin or small hairpin RNA (shRNA), and small molecules which interfere with or inhibit expression of a target gene by RNA interference (RNAi).

The use of siRNAs and siRNA-based technologies (for example, shRNA-expression vectors) has proven to be a powerful tool for the silencing of gene expression in a sequence-specific manner and has been found to be amenable to a wide variety of mammalian cell types and tissues. Not only have siRNAs proven to be effective for the dissection of gene function, but their application as a therapeutic modality is being aggressively investigated.

siRNA is as an agent that functions to inhibit expression of a target gene, e.g., PKK, by RNAi. An siRNA may be chemically synthesized, produced by in vitro transcription (for subsequent isolation and administration), or it may be expressed within a target cell where it is to have its intended effect (e.g., B cell lymphoma or plasma cell myeloma).

siRNA against PKK has been previously reported (Adams et al., "Regulation of NF-κB Activity and Keratinocyte Differentiation by the RIP4 Protein: Implications for Cutaneous Wound Repair," J Invest. Dermatology 127:538-544 (2007); U.S. Patent Application Publ. No. 20040048305 to Kapeller-Libermann, each of which is hereby incorporated by reference in its entirety. Exemplary siRNAs include, without limitation, those identified as #9, #10, and #11 in U.S. Patent Application Publ. No. 20040048305 to Kapeller-Libermann as follows:

9, targeting AAGAACATCCTGCACATCATG, SEQ ID NO: 1, beginning at residue 679 of the RIP4 sequence, with the following structure:

```
                                      SEQ ID NO: 2
Sense      5'-AAGAACAUCCUGCACAUCAUGdTdT-3'

SEQ ID NO: 3
anti-Sense 3'-dTdTUUCUUGUAGGACGUGUAGUAC-5'
```

10, targeting AAGAAGATGGAGATGGCCAAG, SEQ ID NO: 4, beginning at residue 211 of the RIP4 sequence, with the following structure:

```
                                    SEQ ID NO: 5
Sense         5'-AAGAAGAUGGAGAUGGCCAAGdTdT-3'

SEQ ID NO: 6
anti-Sense    3'-dTdTUUCUUCUACCUCUACCGGUUC-5'
```

11 targeting AACCTTCAACCAGCGATCTGG, SEQ ID NO: 7, beginning at residue 1181 of the RIP4 sequence, with the following structure:

```
                                    SEQ ID NO: 8
Sense         5'-AACCUUCAACCAGCGAUCUGGdTdT-3'

SEQ ID NO: 9
anti-Sense    3'-dTdTUUGGAAGUUGGUCGCUAGACC-5'
``` siRNAs also include small hairpin (also called stem loop) RNAs (shRNAs). shRNAs may be composed of a short (e.g., about 19 to about 25 nucleotide) antisense strand, followed by a nucleotide loop of about 5 to about 9 nucleotides, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart et al., "Lentivirus-delivered Stable Gene Silencing by RNAi in Primary Cells," *RNA* 4:493-501 (2003), which is hereby incorporated by reference in its entirety).

According to one embodiment, the shRNA molecule is selected from the group consisting of:

```
GGCCCACCTTCCAAGAAATTA,      (SEQ ID NO: 10)

CGTTCGTTTCTCGTTGCCTAA,      (SEQ ID NO: 11)
and

GCACGATGTATACAGCTTTGC.      (SEQ ID NO: 12)
```

A viral-mediated delivery mechanism may also be employed to deliver siRNAs to cells in vitro and in vivo as described in Xia et al, "siRNA-mediated Gene Silencing in vitro and in vivo," *Nat Biotechnol* 20(10):1006-1010 (2002), which is hereby incorporated by reference in its entirety). Plasmid- or viral-mediated delivery mechanisms of shRNA may also be employed to deliver shRNAs to cells in vitro and in vivo as described in Rubinson et al., "A Lentivirus-based System to Functionally Silence Genes in Primary Mammalian Cells, Stem Cells and Transgenic Mice by RNA Interference," *Nat Genet* 33:401-406 (2003); Stewart et al., "Lentivirus-delivered Stable Gene Silencing by RNAi in Primary Cells," *RNA* 9:493-501 (2003), each of which is hereby incorporated by reference in its entirety).

As used herein, the term "vector" refers to a nucleic acid molecule capable of transporting another nucleic acid to which it has been linked. One type of vector is a plasmid, which refers to a circular double stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host or target cell upon introduction therein, and thereby are replicated along with the host or target cell genome. Moreover, certain vectors are capable of directing the expression of genes to which they are operatively linked. Such vectors are referred to herein as "recombinant expression vectors", or more simply "expression vectors." In general, expression vectors of utility in recombinant DNA techniques are often in the form of plasmids or infective transformation vectors.

Within an expression vector, "operably linked" is intended to mean that the nucleotide sequence of interest is linked to the regulatory sequence(s) in a manner that allows for expression of the desired nucleotide sequence (e.g., in an in vitro transcription/translation system or in a target cell when the vector is introduced into the target cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990), which is hereby incorporated by reference in its entirety. Regulatory sequences include those that direct constitutive expression of a nucleotide sequence in many types of host cell and those that direct expression of the nucleotide sequence only in certain host cells (e.g., tissue-specific regulatory sequences). Furthermore, the siRNAs may be delivered by way of a vector comprising a regulatory sequence to direct synthesis of the siRNAs of the invention at specific intervals, over a specific time period, or only under certain conditions (i.e., inducible). It will be appreciated by those skilled in the art that the design of the expression vector can depend on such factors as the choice of the target cell, the level of expression of siRNA desired, and the like.

In the present invention, expression vectors designed to express the RNAi in the lymphomatic B cells or myeloma plasma cells should include a promoter operable in these cells. Suitable promoters of this type include, without limitation, any constitutive promoters operable in mammalian cells (e.g., SV40, MMTV, metallothionein-1, adenovirus Ela, CMV, immediate early, immunoglobulin heavy chain promoter and enhancer, and RSV-LTR), B cell specific promoters (e.g., promoters from the B29 and mbl genes, and EBV C promoter) (Omori and Wall, "Multiple Motifs Regulate the B-Cell-Specific Promoter of the B29 Gene," *Proc. Natl Acad Sci USA* 90:11723-11727 (1993); Contreras-Brodin et al., "B Cell-specific Activation of the Epstein—Ban Virus-encoded C Promoter Compared with the Wide-range Activation of the W Promoter," *J Gen Virol* 77:1159-1162 (1996), each of which is hereby incorporated by reference in its entirety), as well as inducible promoters (e.g., Tet-O, ecdysone inducible vectors, etc.) (Wang et al., "Stable and Controllable RNA Interference: Investigating the Physiological Function of Glutathionylated Actin," *Proc. Natl. Acad Sci USA* 100:5103-5106 (2003), which is hereby incorporated by reference in its entirety).

From the foregoing, it should be appreciated that the present invention encompasses both gene therapy approaches and non-gene therapy approaches for the treatment of B cell lymphomas and myelomas, and the cell death of the lymphomatic B cells and myeloma plasma cells. Regardless of the approach, they both involve delivery of the therapeutic agent to the cells of interest so that the therapeutic agents, whether directly acting on PKK or modulating PKK expression levels, can have their desired effect.

The therapeutic agent, regardless of its mode of action, is intended to be administered to a patient, preferably in the form of a pharmaceutical composition that also includes a pharmaceutically-acceptable carrier. The pharmaceutical composition may be in a liquid or solid dosage form including, but not limited to, tablets, capsules, powders, solutions, suspensions, or emulsions.

The therapeutic agent of the present invention, and thus the pharmaceutical compositions of the present invention, can be administered orally, parenterally, subcutaneously, intravenously, intramuscularly, intraperitoneally, by intranasal instillation, by implantation, by intracavitary or intravesical instillation, intraocularly, intraarterially, intralesionally, transdermally, by application to mucous membranes (such as, that of the nose, throat, and bronchial tubes), or by introduction into one or more lymph nodes. In certain embodiments, the therapeutic agent is administered directly into a site containing the B cell lymphoma or myeloma plasma cells to be treated. In other embodiments, the therapeutic agent is administered systemically. In further embodiments, a combination of different administration routes can be employed to effectively target the lymphoma or myeloma.

For the use in accordance with the invention, the appropriate dosage of the therapeutic agent, e.g. inhibitor of PKK activity, will, of course, vary depending upon, for example, the particular agent to be employed, the host, the mode of administration and the severity of the B cell malignancy being treated, and the effects desired. Satisfactory results are generally indicated to be obtained at dosages from about 0.1 mg to about 1000 mg, preferably from 1 to 100 mg, more preferably 20-50 mg. For example dosages can be 0.3 mg/kg body weight, 1 mg/kg body weight, 3 mg/kg body weight, 5 mg/kg body weight or 10 mg/kg body weight, or within the range of 1-10 mg/kg. Administration may be in a single dose or in several doses over a period of time as long as may be indicated in relation to the time the disease is clinically evident or prophylactically to suppress further clinical relapse, for example a dose from about 5 up to about 100 mg, may be administered once a month, until control or amelioration of the disease is achieved. A preferred dosage regimen comprises administration of 20-50 mg of the therapeutic inhibitor of PKK activity every two weeks or once a month. An exemplary treatment regime entails administration once per week, once every two weeks, once every three weeks, once every four weeks, once a month, once every 3 months or once every three to 6 months.

The therapeutic agent of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, the therapeutic agents may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

The therapeutic agent may also be administered parenterally. Solutions or suspensions of these therapeutic agents can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, saline, ethanol, polyol (e.g., glycerol, propylene glycol, and liquid polyethylene glycol), suitable mixtures thereof, and vegetable oils.

The therapeutic agents of the present invention may also be administered directly to the airways in the form of an aerosol or via a lung surfactant formulation. For use as aerosols, the inhibitors of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer. A number of commercially available lung surfactant formulations exist, including synthetic surfactant formulations and exogenous formulations.

It is also contemplated that the compositions of the invention can be delivered by various transdermal drug delivery systems, such as transdermal patches as is known in the art.

Persons of skill in the art are readily able to test and assess optimal dosage schedules based on the balance of efficacy and any undesirable side effects. The optimal dosage of each type of inhibitor will vary, of course, and the minimal effective dose will be administered for therapeutic regimen.

Sustained release formulations include implantable devices that include a slow-dissolving polymeric matrix and the therapeutic agent of the invention retained within the polymeric matrix. The matrix can be designed to deliver substantially the entire payload of the vehicle over a predetermined period of time, such as about one to two weeks or about one to three months. These sustained release formulations can be used to deliver nucleic acids or non-nucleic acid therapeutic agents.

In addition, the therapeutic agents of the present invention can be administered in using a delivery vehicle for passive or targeted delivery to particular cells that are known to possess the target RNA molecule. Any suitable passive or targeted delivery vehicle can be employed, including liposomes, polymeric nanoparticles, chimeric proteins, polyethylene glycol conjugates, and oligoarginine.

One approach for delivering agents into cells involves the use of liposomes. Basically, this involves providing a liposome which includes agent to be delivered, and then contacting the target cell with the liposome under conditions effective for delivery of the agent into the cell.

Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature. Current methods of drug delivery via liposomes require that the liposome carrier ultimately become permeable and release the encapsulated drug at the target site. This can be accomplished, for example, in a passive manner wherein the liposome bilayer degrades over time through the action of various agents in the body. Every liposome composition will have a characteristic half-life in the circulation or at other sites in the body and, thus, by controlling the half-life of the liposome composition, the rate at which the bilayer degrades can be somewhat regulated.

In contrast to passive drug release, active drug release involves using an agent to induce a permeability change in the liposome vesicle. Liposome membranes can be constructed so that they become destabilized when the environment becomes acidic near the liposome membrane (see, e.g., Wang et al., "pH-sensitive Immunoliposomes Mediate Target-cell-specific Delivery and Controlled Expression of a Foreign Gene in Mouse," Proc. Natl. Acad. Sci. USA 84:7851-7855 (1987), which is hereby incorporated by reference in its entirety). When liposomes are endocytosed by a target cell, for example, they can be routed to acidic endosomes which will destabilize the liposome and result in drug release.

Alternatively, the liposome membrane can be chemically modified such that an enzyme is placed as a coating on the membrane, which enzyme slowly destabilizes the liposome. Since control of drug release depends on the concentration of enzyme initially placed in the membrane, there is no real effective way to modulate or alter drug release to achieve "on demand" drug delivery. The same problem exists for pH-sensitive liposomes in that as soon as the liposome vesicle comes into contact with a target cell, it will be engulfed and a drop in pH will lead to drug release.

This liposome delivery system can also be made to accumulate at a target organ, tissue, or cell via active targeting (e.g., by incorporating an antibody or hormone on the surface of the liposomal vehicle). This can be achieved according to known methods. Humanized antibodies that are specific for an epitope of CD22 expressed on B-cell lymphomas and leukemias are described in U.S. Pat. No. 5,789,554 to Leung et al., which is hereby incorporated by reference in its entirety.

Antibodies specific for myeloma cell markers can also be used, such as antibodies to CD40 (U.S. Patent Application Publ. No. 20070218060 to Long et al., which is hereby incorporated by reference), CD38 (U.S. Patent Application Publ. No. 20040141982 to Lust et al.; Ellis et al., "Engineered anti-CD38 Monoclonal Antibodies for Immunotherapy of Multiple Myeloma," J Immunol 155(2):925-937 (1995), each of which is hereby incorporated by reference in its entirety), CD138 (Dhodapkar et al., "Syndecan-1 (CD138) in Myeloma and Lymphoid Malignancies: A Multifunctional Regulator of Cell Behavior Within the Tumor Microenvironment," Leuk Lymphoma 34(1-2):35-43 (1999), which is hereby incorporated by reference in its entirety), CD56 (U.S. Pat. No. 7,371,576 to Tsang et al., which is hereby incorporated by reference in its entirety), and CD28 (Bahlis et al., "CD28-mediated Regulation of Multiple Myeloma Cell Proliferation and Survival," Blood 109(10):5002-5010 (2007), which is hereby incorporated by reference in its entirety).

Different types of liposomes can be prepared according to Bangham et al., "Diffusion of Univalent Ions Across the Lamellae of Swollen Phospholipids," J. Mol. Biol. 13:238-252 (1965); U.S. Pat. No. 5,653,996 to Hsu et al.; U.S. Pat. No. 5,643,599 to Lee et al.; U.S. Pat. No. 5,885,613 to Holland et al.; U.S. Pat. No. 5,631,237 to Dzau et al.; and U.S. Pat. No. 5,059,421 to Loughrey et al., each of which is hereby incorporated by reference in its entirety.

An alternative approach for delivery of proteins or polypeptide agents (e.g., dominant negative PKK fragments) involves the conjugation of the desired protein or polypeptide to a polymer that is stabilized to avoid enzymatic degradation of the conjugated protein or polypeptide. Conjugated proteins or polypeptides of this type are described in U.S. Pat. No. 5,681,811 to Ekwuribe, which is hereby incorporated by reference in its entirety.

Yet another approach for delivery of proteins or polypeptide agents involves preparation of chimeric proteins according to U.S. Pat. No. 5,817,789 to Heartlein et al., which is hereby incorporated by reference in its entirety. The chimeric protein can include a ligand domain and the polypeptide agent (e.g., dominant negative PKK fragments). The ligand domain is specific for B-cells, particularly lymphomas and myelomas. These include CD20-specific antibodies like rituximab (described below) and the humanized antibodies that are specific for B-cell lymphomas and leukemias as described in U.S. Pat. No. 5,789,554 to Leung et al., which is hereby incorporated by reference in its entirety, as well as the antibodies specific for myeloma cell markers (noted above). Thus, when the chimeric protein is delivered intravenously or otherwise introduced into blood or lymph, the chimeric protein will adsorb to the targeted cell, and the targeted cell will internalize the chimeric protein.

Polymeric nanoparticles can be targeted to cell-surface marked using aptamers designed using the SELEX procedure (Farokhzad et al., "Targeted Nanoparticle-aptamer Bioconjugates for Cancer Chemotherapy in vivo," Proc. Natl. Acad. Sci. USA 103(16):6315-6320 (2006), which is hereby incorporated by reference in its entirety). Nanoparticles and microparticles may comprise a concentrated core of drug that is surrounded by a polymeric shell (nanocapsules) or as a solid or a liquid dispersed throughout a polymer matrix (nanospheres). General methods of preparing nanoparticles and microparticles are described by Soppimath et al., "Biodegradable Polymeric Nanoparticles as Drug Delivery Devices," J. Control Release 70(1-2):1-20 (2001), which is hereby incorporated by reference in its entirety. Other polymeric delivery vehicles that may be used include block copolymer micelles that comprise a drug containing a hydrophobic core surrounded by a hydrophilic shell; they are generally utilized as carriers for hydrophobic drugs and can be prepared as found in Allen et al., "Colloids and Surfaces," Biointerfaces 16(1-4):3-27 (1999), which is hereby incorporated by reference in its entirety. Polymer-lipid hybrid systems consist of a polymer nanoparticle surrounded by a lipid monolayer. The polymer particle serves as a cargo space for the incorporation of hydrophobic drugs while the lipid monolayer provides a stabilizing interference between the hydrophobic core and the external aqueous environment. Polymers such as polycaprolactone and poly(D,L-lactide) may be used while the lipid monolayer is typically composed of a mixture of lipids. Suitable methods of preparation are similar to those referenced above for polymer nanoparticles. Derivatized single chain polymers are polymers adapted for covalent linkage of a biologically active agent to form a polymer-drug conjugate. Numerous polymers have been proposed for synthesis of polymer-drug conjugates including polyaminoacids, polysaccharides such as dextrin or dextran, and synthetic polymers such as N-(2-hydroxypropyl)methacrylamide (HPMA) copolymer. Suitable methods of preparation are detailed in Veronese et al, "Bioconjugation in Pharmaceutical Chemistry," IL Farmaco 54(8):497-516 (1999), which is hereby incorporated by reference in its entirety.

The therapeutic agents can also be administered as a conjugate with a pharmaceutically acceptable water-soluble polymer moiety. By way of example, a polyethylene glycol conjugate is useful to increase the circulating half-life of the therapeutic agent, and to reduce the immunogenicity of the molecule. Specific PEG conjugates are described in U.S. Patent Application Publ. No. 20060074200 to Daugs et al., which is hereby incorporated by reference in its entirety. Liquid forms, including liposome-encapsulated formulations, are illustrated by injectable solutions and oral suspensions. Exemplary solid forms include capsules, tablets, and controlled-release forms, such as a miniosmotic pump or an implant. Other dosage forms can be devised by those skilled in the art, as shown, for example, by Ansel and Popovich, PHARMACEUTICAL DOSAGE FORMS AND DRUG DELIVERY SYSTEMS, 5$^{th}$ Edition (Lea & Febiger 1990), Gennaro (ed.), REMINGTON'S PHARMACEUTICAL SCIENCES, 19$^{th}$ Edition (Mack Publishing Company 1995), and by Ranade and Hollinger, DRUG DELIVERY SYSTEMS (CRC Press 1996), each of which is hereby incorporated by reference in its entirety.

Peptide conjugates that can be used to augment cellular uptake are known in the art, and include HIV-Tat polypeptide fragments, oligoarginine, and other peptide conjugates as described in de Coupade et al., "Novel Human-derived Cell-penetrating Peptides for Specific Subcellular Delivery of Therapeutic Biomolecules," Biochem J. 390(Pt 2):407-418 (2005); U.S. Patent Application Publ. No. 20030032593 to Wender et al., each of which is hereby incorporated by reference in its entirety.

Gene therapy approaches of practicing the present invention can be delivered to a subject in a number of ways known in the art, including through the use of gene therapy vectors and methods as described above.

The pharmaceutical compositions of the present invention can be administered alone or in combination with other therapies, including without limitation chemotherapy agents, immunotherapy agents, radiation treatments, or combinations thereof. It is contemplated that the therapeutic agents of the present invention can be administered together with any other B cell lymphoma therapy or myeloma therapy. When two or more therapeutic agents are administered together, they can be administered simultaneously or with some delay between administration thereof (i.e., according to an optimized delivery schedule). Standard dosages of such known therapeutic agents can be administered.

Exemplary immunotherapy agents for lymphomas include rituximab (Rituxan®), Bexxar® (tositumomab with $^{131}$I) (Corixia Corp.), and Zevalin™ (ibritumomab tiuxetan with $^{111}$In or $^{90}$Y). Rituximab works by selectively depleting CD20$^+$ B cells. The therapeutic effectiveness of rituximab is described in Collins-Burow et al., "Rituximab and its Role as Maintenance Therapy in non-Hodgkin Lymphoma," Expert Rev Anticancer Ther 7(3):257-73 (2007); Marcus et al., "The Therapeutic Use of Rituximab in non-Hodgkin's Lymphoma," Eur J Haemotol Suppl (67):5-14 (2007), each of which is hereby incorporated by reference in its entirety.

Other B cell lymphoma therapies include, without limitation, chemotherapies such as bleomycin (Blenoxane®), carboplatin (Paraplatin®), chlorambucil (Leukeran®), cyclophosphamide (Cytoxan®), cladribine, cytarabine (Cytosar-U®), dacarbazine (DTIC-Dome®), dexamethasone (Decadron®), doxorubicin (Adriamycin®), etoposide (Etopophos®), fludarabine (Fludara®), ifosfamide (Ifex®), methotrexate, prednisone, vincristine (Oncovin®), vinblastine, and CHOP combination therapy (described above).

Exemplary immune modulators or immunotherapy agents for myelomas include thalidomide, lenalidomide, bortezomib, and Neovastat (see Kyle and Rajkumar, "Multiple Myeloma" Blood 111(6):2962-2972 (2008), which is hereby incorporated by reference in its entirety).

EXAMPLES

The following examples are provided to illustrate embodiments of the present invention but are by no means intended to limit its scope.

Materials and Methods for Examples 1-7

Cell Culture, Antibodies, and Reagents

Four human Diffuse Large B Cell Lymphoma (DLBCL) cell lines: OCI-Ly10, OCI-Ly3 (ABC-like DLBCL); OCI-Ly7 and SUDHL-6 cells (GC-like DLBCL) were cultured as described (Davis et al., "Constitutive Nuclear Factor κB Activity is Required for Survival of Activated B Cell-like Diffuse Large B Cell Lymphoma Cells," J Exp Med 194: 1861-1874 (2001), which is hereby incorporated by reference in its entirety), except that fetal bovine serum (10% or as indicated) was used. To generate SUDHL-6 cells that stably express the N-terminal kinase domain (PKK-N, amino acids 1 to 320) of PKK (Chen et al., "Protein Kinase C-associated Kinase (PKK), a Novel Membrane-associated, Ankyrin Repeat-containing Protein Kinase," J Biol Chem 276:21737-21744 (2001); Moran et al., "Protein Kinase C-associated Kinase can Activate NFκB in Both a Kinase-dependent and a Kinase-independent Manner," J Biol Chem 278:21526-21533 (2003), each of which is hereby incorporated by reference in its entirety), the cells were infected with pMIG retroviral vector (generously provided by Dr. Warren Pear, University of Pennsylvania) that expresses Flag-tagged PKK-N and GFP. PKK-N-expressing cells were then sorted through GFP expression. Human BAFF was purchased from PeproTech (Rocky Hill, N.J.). Antibodies against human IKKα, RelB, casepase3 and PARP were purchased from Santa Cruz Biotechnology. Anti-human p52 antibody was purchased from Upstate Biotechnologies. Antibodies specific for IκBα, phospho-IκBα (p-Ser$^{32}$), IKKβ, phospho-IKKα (p-Ser$^{176/180}$)/IKKβ (p-ser$^{177/181}$) were from Cell Signaling Technology. Antibody specific for Flag tag was from Sigma.

RNA Interference using Small Hairpin RNA (shRNA)

PKK expression was suppressed by RNA interference with small hairpin RNAs (shRNA) specific for human PKK mRNA. Three targeting sequences (shPKK-1: 5'-GGC-CCACCTTCCAAGAAATTA, SEQ ID NO: 10; shPKK-2: 5'-CGTTCGTTTCTCGTTGCCTAA, SEQ ID NO: 11; and shPKK-3: 5'-GCACGATGTATACAGCTTTGC, SEQ ID NO: 12) were selected and cloned into either the retroviral pRetro-H1 vector (referred to as shPKK-1, shPKK-2 and shPKK-3, respectively), or the lentiviral vector plenty-hu6B (referred to as L-shPKK-1, L-shPKK-3 and L-shPKK-3, respectively) (Cellogenetics Inc.). A random hairpin sequence (5'-GTTCTCCGAACGAACGTGTCACG, SEQ ID NO: 13) was also cloned into these two vectors and referred to as shControl and L-shControl, respectively. Lentiviruses expressing L-shControl or an L-shPKK were produced using ViraPower lentiviral expression system following the protocol suggested by the manufacturer (Invitrogen). To generate SUDHL-6 or OCI-Ly7 cells that stably express shControl or a shPKK, the cells were infected with the recombinant retroviruses, produced using amphotropic viral packaging cell line (kindly provided by Dr. GaryNolan, Stanford University). The transduced cells were selected with puromycin (0.5 ug/ml) for two weeks. After the drug selection, bulk infected cells were used in the experiments to avoid clonal variations.

To assess the efficiency of PKK knockdown by the PKK-specific shRNA constructs, total RNA was isolated using RNeasy kit (Qiagen), and the standard RT-PCR procedure was performed using the reagents from Invitrogen. The primers (5'-ATGGAGGGCGACGGCGGGACC-3', SEQ ID NO: 14; and 5'-CAGGGAGCCCGTCTCCATGT-3', SEQ ID NO: 15) specific for human PKK were used for PCR reaction.

Transfection, Immunoprecipitation, Western Blot Analysis and in vitro Kinase Assays Preparation of Cell Lysates, Immunoprecipitation and Western Blot analysis were performed as previously described (Chen et al., "Protein Kinase C-associated Kinase (PKK), a Novel Membrane-associated, Ankyrin Repeat-containing Protein Kinase," *J Biol Chem* 276:21737-21744 (2001); Zhao et al., "Expression of NPAT, a Novel Substrate of Cyclin E-CDK2, Promotes S-phase Entry," *Genes Dev* 12:456-461 (1998), each of which is hereby incorporated by reference in its entirety). For in vitro kinase assays, the lysates from SUDH-6 expressing shControl and shPKK-1, respectively, were immunoprecipitated with an antibody specific for human IKKβ. Half of the immunoprecipitates were used for analyzing the amounts of immunoprecipitated IKKβ by western blotting. The other half was used for in vitro kinase assays, which were carried out in the presence of [γ-$^{32}$P]ATP essentially as previously described (Chen et al., "Protein Kinase C-associated Kinase (PKK), a Novel Membrane-associated, Ankyrin Repeat-containing Protein Kinase," *J Biol Chem* 276:21737-21744 (2001); Zhao et al., "Expression of NPAT, a Novel Substrate of Cyclin E-CDK2, Promotes S-phase Entry," *Genes Dev* 12:456-461 (1998), each of which is hereby incorporated by reference in its entirety). Purified GST-IκBα (amino acids 1-54) was used as the substrate for the precipitated IKK complex. The kinase reaction products were analyzed by autoradiography following SDS-polyacrylamide gel electrophoresis.

Cell Viability and Apoptosis Assays

Cell viability was measured by the MTT assays as described by the manufacturer (Roche). The apoptosis assays were performed using the Annexin V-PE apoptosis detection kit I (BD Bioscience), and at least 10,000 events were recorded. The FACS data were analyzed using Flojo5.1 software (Becton Dickson).

In Vivo Xenografts

All animal experiments were performed in compliance with institutional guidelines and with approval of our institutional Animal Care and Use Committee (IACUC). NOD/SCID male mice age 6-8 weeks were obtained from Jackson Laboratories (Bar Harbor, Me.). 5×10$^6$ of OCI-Ly7 cells stably expressing shControl or shPKK-1, respectively, were injected subcutaneously into NOD/SCID mice (n=4, each). The tumor size was measured at different days post-implantation. The volumes of the tumors were calculated according to the formula: tumor volume=4/3πx(length/2)×(width/2)× (height/2). Statistic significance of the difference was analyzed by standard student T test.

Example 1

PKK Regulates NF-κB Activity in Human DLBCL Cells

To investigate whether PKK regulates NF-κB activity in DLBCL cells, the effect of PKK overexpression on NF-κB activation in SUDHL-6 cells, a human GCB DLBCL cell line that has previously been shown to have low constitutive NF-κB activity was examined first (Davis et al., "Constitutive Nuclear Factor κB Activity is Required for Survival of Activated B Cell-like Diffuse Large B Cell Lymphoma Cells," *J Exp Med* 194:1861-1874 (2001), which is hereby incorporated by reference in its entirety). SUDHL-6 cells that stably express N-terminal kinase domain of PKK (PKK-N), which was previously shown to be capable of activating NF-κB reporter (Moran et al., "Protein Kinase C-associated Kinase can Activate NFκB in Both a Kinase-dependent and a Kinase-independent Manner," *J Biol Chem* 278:21526-21533 (2003), which is hereby incorporated by reference in its entirety), exhibit higher levels of IκBα phosphorylation (FIG. 1A), a hallmark of NF-κB activation (Hayden et al., "Signaling to NF-κB," *Genes Dev* 18:2195-2224 (2004); Karin, "NF-κB and Cancer: Mechanisms and Targets," *Mol Carcinog* 45:355-361 (2006); Scheidereit, "IκB Kinase Complexes: Gateways to NF-κB Activation and Transcription," *Oncogene* 25:6685-6705 (2006), each of which is hereby incorporated by reference in its entirety). In addition, PKK-expressing cells showed higher levels of IKK phosphorylation at the two conserved serine residues (Ser$^{176}$ and Ser$^{180}$ in IKKα and Ser$^{177}$ and Ser$^{181}$ in IKKβ) (FIG. 1A), which is known to be required for IKK activation (Hu et al., "IKKα Controls Formation of the Epidermis Independently of NF-κB," *Nature* 410:710-714 (2001); Delhase et al., "Positive and Negative Regulation of IκB Kinase Activity Through IKKβ Subunit Phosphorylation," *Science* 284:309-313 (1999); Ling et al., "NF-κB-inducing Kinase Activates IKK-α by Phosphorylation of Ser-176," *Proc Natl Acad Sci USA* 95:3792-3797 (1998), each of which is hereby incorporated by reference in its entirety). These results indicate that PKK can activate NF-κB in DLBCL cells.

Next it was determined whether PKK is required for NF-κB activation in DLBCL cells. For this purpose, the effect of suppression of PKK on NF-κB activity in OCI-Ly10 cells, a human ABC DLBCL cell line that has been shown to exhibit high constitutive NF-κB activity, was examined (Davis et al., "Constitutive Nuclear Factor κB Activity is Required for Survival of Activated B Cell-like Diffuse Large B Cell Lymphoma Cells," *J Exp Med* 194:1861-1874 (2001), which is hereby incorporated by reference in its entirety). A recombinant lentivirus was prepared that expresses a PKK-specific shRNA (L-shPKK-1) and the green fluorescent protein (GFP). As a control, a lentivirus that expresses a random hairpin sequence and the GFP protein (L-shControl) was also prepared. Forty-eight hours after lentiviral infection, approximately 70-80% of the OCI-Ly10 cells were GFP-positive, and the two viruses yield comparable infection efficiency. The expression of PKK was effectively suppressed in the OCI-Ly10 cells by the L-shPKK-1 (FIG. 1B). Suppression of PKK expression resulted in inhibition of NF-κB activity in OCI-Ly10 cells as indicated by the decreases in IκBα phosphorylation (FIG. 1B). Furthermore, PKK knockdown inhibited IKK phosphorylation (FIG. 1B). To gain more direct evidence that PKK is required for NF-κB activity in OCI-Ly10 cells, NF-κB DNA-binding activity in control cells and the cells expressing a PKK-specific shRNA was compared. In these experiments, an additional shPKK, L-shPKK-2, that targets a different PKK mRNA sequence from the one targeted by L-shPKK-1 was included, so that the possibility of the "off-target" effect from the use of a single shPKK could be minimized. PKK knockdown by either shPKK led to significant decreases in the DNA binding activity of several members of the NF-κB family (FIG. 1C). These results suggest that PKK regulates NF-κB activation in ABC DLBCL cells through modulating IKK activation.

It was also investigated whether PKK is required for NF-κB activity in GCB DLBCL cells. To knockdown the expression of PKK in SUDHL-6 and OCI-Ly7 cells, two GCB DLBCL cell lines, cells were generated that stably express either a small hairpin RNA specific for PKK (shPKK-1) or a control small hairpin RNA (shControl). Expression of an shPKK effectively inhibited expression of PKK in both SUDHL-6 and OCI-Ly7 cells (FIGS. 1D-E). Suppression of PKK expression apparently had little effect on the constitutive NF-κB activity in these cells cultured in the normal growth (10% serum) medium. In contrast, PKK knockdown in these cells cultured in serum-free medium yielded a moderate, but reproducible, decrease in the basal NF-κB activity, as indicated by the increase in iκbα protein level and the decreases in the expression of several known NF-κB targets (Bren et al., "Transcription of the RelB Gene is Regulated by NF-κB," *Oncogene* 20:7722-7733 (2001); Lombardi et al., "Structural and Functional Characterization of the Promoter Regions of the NFκB2 gene," *Nucleic Acids Res* 23:2328-2336 (1995); Zong et al., "The Prosurvival Bcl-2 Homolog Bfl-1/A1 is a Direct Transcriptional Target of NF-κB that Blocks TNFα-induced Apoptosis," *Genes Dev* 13:382-387 (1999); Grumont et al., "Rel-dependent Induction of Al Transcription is Required to Protect B Cells from Antigen Receptor Ligation-induced Apoptosis," *Genes Dev* 13:400-411 (1999), each of which is hereby incorporated by reference in its entirety) (FIGS. 1D-E). Furthermore, PKK knockdown also results in decrease of NF-κB DNA-binding activity of p65 and p50 (FIG. 1F). Thus, PKK is also required for basal NF-κB activity in GCB DLBCL cells. The lack of apparent effect of PKK knockdown on NF-κB activity in SUDHL-6 and OCI-Ly7 cells cultured in 10% serum may reflect that PKK regulates NF-κB activation by some but not all signaling pathways in these cells. Taken together, the above results indicate that PKK regulates NF-κB activation in DLBCL cells and that PKK functions upstream of IKK activation.

Example 2

PKK Regulates NF-κB Activation Induced by BAFF in DLBCL Cells

Figure 2E:
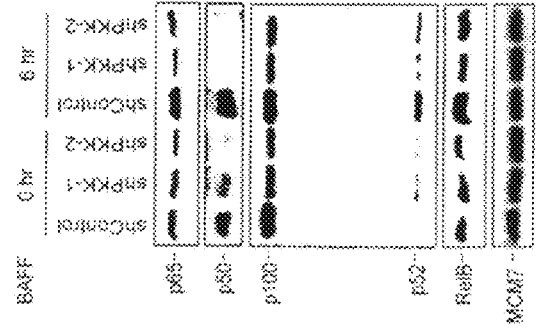

It was examined which stimulus requires PKK for NF-κB activation in DLBCL cells. The observation that PKK knockdown inhibited NF-κB activity in cells cultured in serum-free media suggest that PKK may regulate NF-κB activation in these cells by an autocrine signal(s). As BAFF induces NF-κB activation in both normal and malignant B lymphocytes, and a variety of malignant B cells produce BAFF as a critical autocrine survival factor (Sutherland et al., "Targeting BAFF: Immunomodulation for Autoimmune Diseases and Lymphomas," *Pharmacol Ther* 112:774-786 (2006); He et al., "Lymphoma B Cells Evade Apoptosis Through the TNF Family Members BAFF/BLyS and APRIL," *J Immunol* 172:3268-3279 (2004); Novak et al., "Aberrant Expression of B-lymphocyte Stimulator by B Chronic Lymphocytic Leukemia Cells: A Mechanism for Survival," *Blood* 100:2973-2979 (2002); Fu et al., "Constitutive NF-κB and NFAT Activation Leads to Stimulation of the BLyS Survival Pathway in Aggressive B Cell Lymphomas," *Blood* 107(11):4540-4548 (2006); Endo et al., "BAFF and APRIL Support Chronic Lymphocytic Leukemia B-cell Survival Through Activation of the Canonical NF-κB pathway," *Blood* 109:703-710 (2007), each of which is hereby incorporated by reference in its entirety), it was explored whether PKK regulates NF-κB activation induced by BAFF in DLBCL cells. SUDHL-6 cells express all three known receptors for BAFF (Bossen et al., "BAFF, APRIL and their Receptors: Structure, Function and Signaling," *Semin Immunol* 18:263-275 (2006), which is hereby incorporated by reference in its entirety) (FIG. 2A). BAFF treatment of SUDHL-6 cells expressing the control shRNA (shControl) led to an increase in IκBα phosphorylation (FIG. 2B), nuclear translocation of NF-κB proteins (FIG. 2C), NF-κB DNA-binding activity (FIG. 2D), indicating the activation of NF-κB signaling. In contrast, such increases were severely inhibited in SUDHL-6 cells that express a PKK-specific shRNA (FIGS. 2B-D, and 3A). Similarly, suppression of PKK expression in OCI-Ly7 cells also resulted in inhibition of BAFF-induced NF-κB activation (FIG. 3B), suggesting that requirement for PKK in BAFF-induced NF-κB activation is not limited to SUDHL-6 cells. Consistent with the suggestion that PKK functions upstream of IKK activation, suppression of PKK expression inhibited IKK activation induced by BAFF in SUDHL-6 cells (FIG. 2E). These results demonstrate that PKK plays a critical role in NF-κB activation induced by BAFF in DLBCL cells.

Example 3

PKK is Essential for Survival of ABC DLBCL Cells

It has been shown that constitutive NF-κB activity is essential for the survival of ABC DLBCL cells such as OCI-Ly10 cells (Davis et al., "Constitutive Nuclear Factor κB Activity is Required for Survival of Activated B Cell-like Diffuse Large B Cell Lymphoma Cells," *J Exp Med* 194:1861-1874 (2001); Lam et al., "Small Molecule Inhibitors of IκB Kinase Are Selectively Toxic for Subgroups of Diffuse Large B-cell Lymphoma Defined by Gene Expression Profiling," *Clin Cancer Res* 11:28-40 (2005), each of which is hereby incorporated by reference in its entirety). Given that PKK is crucial for NF-κB activity in these cells (FIGS. 1, 2 and 3), suppression of PKK expression would likely affect the survival of these cells. To test this notion directly, OCI-Ly10 cells with lentiviruses that express either L-shPKK-1 or L-shControl were infected, and then survival of the infected cells was monitored. Since both viruses also express GFP, survival of the infected cells was assessed through flow cytometry analysis of fractions of GFP-positive cells over time after lentiviral infection. The fraction of GFP-positive cells that express L-shPKK-1 was significantly decreased by three days post-infection, while no such decrease was observed for the cells infected with the control virus (FIG. 4A). The slight increase in the GFP-positive fraction in the control cells at three days after infection is probably due to GFP expression in additional cells after two days of viral infection. These results indicate that PKK is essential for survival of OCI-Ly10 cells. To confirm that loss of the GFP-positive cells that express L-shPKK indeed resulted from cell death, the fraction of annexin V-positive cells (apoptotic cells (Koopman et al., "Annexin V for Flow Cytometric Detection of Phosphatidylserine Expression on B Cells Undergoing Apoptosis," *Blood* 84:1415-1420 (1994); Vermes et al., "A Novel Assay for Apoptosis. Flow Cytometric Detection of Phosphatidylserine Expression on Early Apoptotic Cells Using Fluorescein Labeled Annexin V," *J Immunol Methods* 184:39-51

Figure 5B:
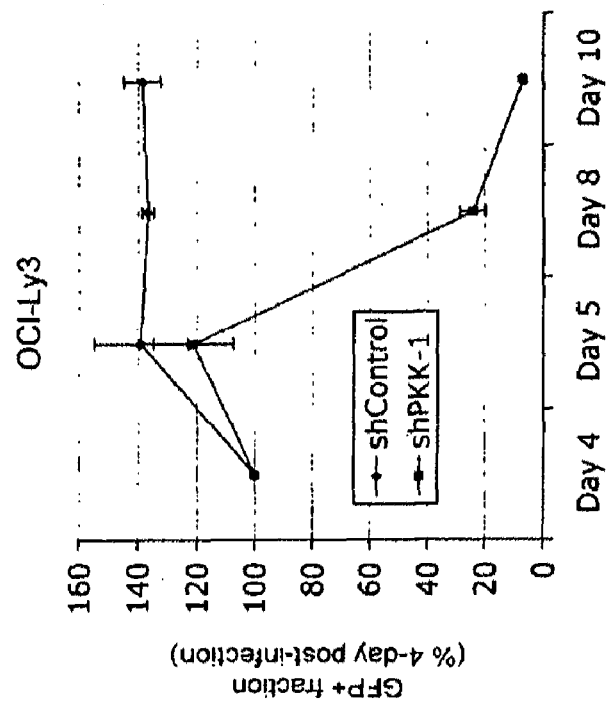
FIGS. 5A-B show that PKK is essential for the survival of ABC DLBCL cells.
Figure 5A:
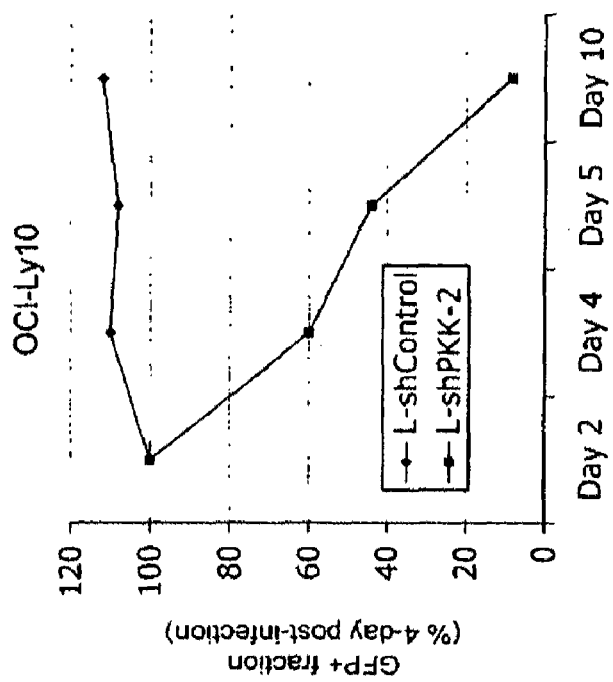

(1995), each of which is hereby incorporated by reference in its entirety)) in the infected (GFP-positive) cells was analyzed. As shown in FIG. 4B, PKK knockdown significantly increased the fraction of annexin V-positive cells, further demonstrating that PKK knockdown results in cell death of OCI-Ly10 cells. Consistent with the annexin V analysis, suppression of PKK expression in OCI-Ly10 cells by LshPKK-1 led to increases in PARP cleavage and activation of caspase-3 (cleaved caspase-3) (FIG. 4C), hallmarks of apoptosis (Nicholson et al., "Identification and Inhibition of the ICE/CED-3 Protease Necessary for Mammalian Apoptosis," *Nature* 376:37-43 (1995); Lazebnik et al., "Cleavage of Poly (ADP-ribose) Polymerase by a Proteinase with Properties like ICE," *Nature* 371:346-347 (1994); Kaufmann et al., "Specific Proteolytic Cleavage of Poly(ADP-ribose) Polymerase: An Early Marker of Chemotherapy-induced Apoptosis," *Cancer Res* 53:3976-3985 (1993), each of which is hereby incorporated by reference in its entirety). PKK knockdown in OCI-Ly10 cells by another PKK-specific shRNA (L-shPKK-2) also led to cell death as indicated by the loss of L-shPKK-2-expressing cells (FIG. 5A), suggesting that the cell death of OCI-Ly10 cells expressing a PKK-specific shRNA resulted most likely from specific suppression of PKK expression rather than the non-specific off-target effect of an shPKK. PKK knockdown also induced cell death of OCI-Ly3 cells, another ABC DLBCL cell line (FIG. 5B). Together, the results demonstrate that PKK is required for survival of ABC DLBCL cells by preventing the cells from apoptosis.

Figure 7:
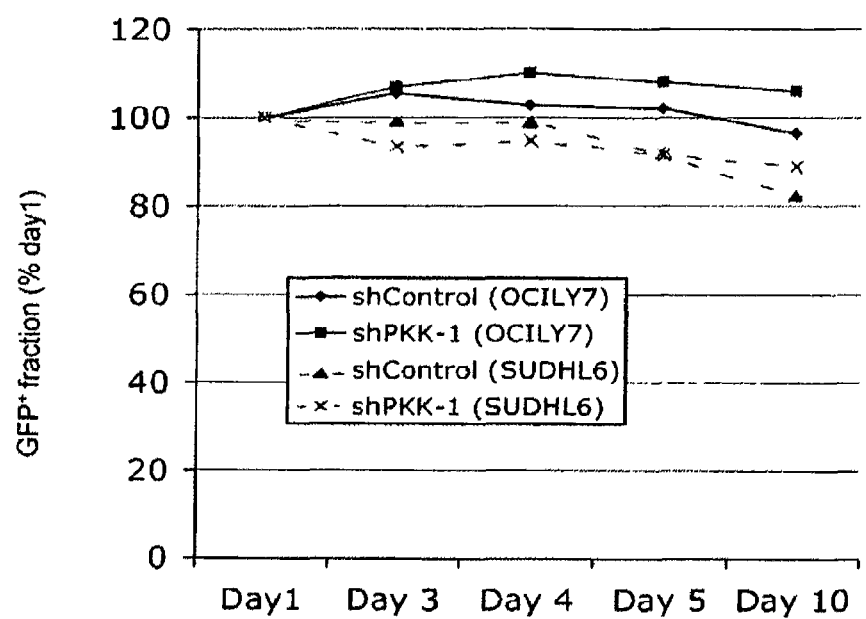
FIG. 7 is a graph showing that PKK is not required for the survival of OCI-Ly7 and SUDHL-6 cells cultured in medium containing 10% serum. OCI-Ly7 or SUDHL-6 cells were infected with the retroviruses (pRetro-H1) that express GFP together with either shControl or shPKK-1. The GFP positive fractions of OCI-Ly7 or SUDHL-6 cells stably expressing either shControl or shPKK-1 were analyzed by flow cytometry at the indicated times. The GFP-positive fractions were normalized to the samples harvested at day 1 of the analysis.
Figure 8:
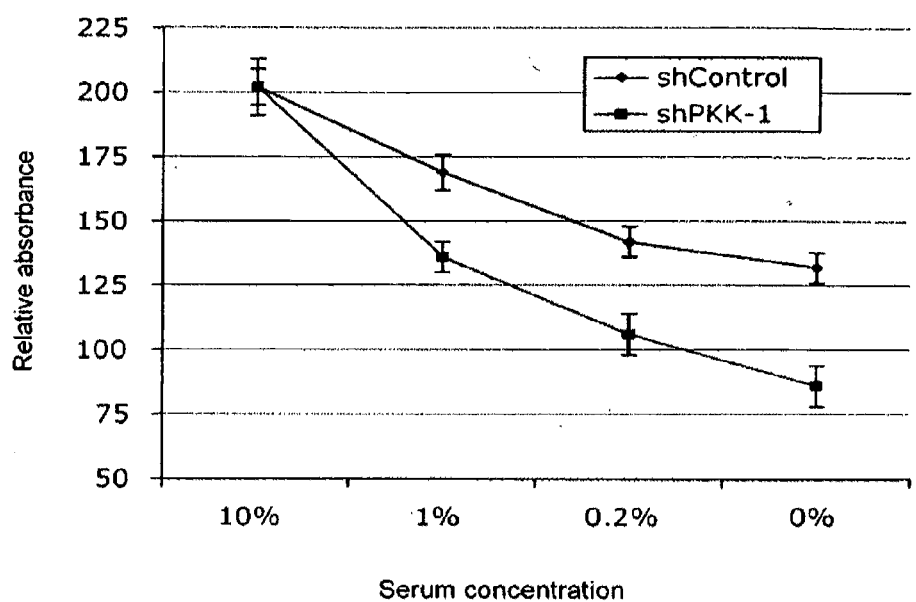
FIG. 8 is a graph showing the effect of PKK knockdown on survival of OCI-Ly7 cells. OCI-Ly7 cells stably expressing shControl or shPKK-1 were cultured in the medium containing indicated concentrations of serum for 24 hours. The live cells were measured by the MTT assay. The results were normalized to the absorbance readings at the time the cells were plated (0 hr), which were arbitrarily set at 100.

The observation that PKK is essential for the survival of ABC DLBCL cells prompted an investigation as to whether PKK is also involved in the survival of GCB DLBCL cells. SUDHL-6 cells were cultured that stably express shControl or shPKK-1 in the medium containing different concentrations of serum. The survival of the cells was measured using MTT assay (Vistica et al., "Tetrazolium-based Assays for Cellular Viability: A Critical Examination of Selected Parameters Affecting Formazan Production," *Cancer Res* 51:2515-2520 (1991); Mosmann, "Rapid Colorimetric Assay for Cellular Growth and Survival: Application to Proliferation and Cytotoxicity Assays," *J Immunol Methods* 65:55-63 (1983), each of which is hereby incorporated by reference in its entirety). Whereas PKK knockdown had little effect on the survival of SUDHL-6 cells cultured in medium containing 10% serum (FIGS. 6A and 7), suppression of PKK expression impairs survival of these cells when cultured in the medium with a low concentration of serum or without serum (FIG. 6B). Similarly, PKK knockdown affected the survival of OCI-Ly7 cells only when they were cultured with low concentrations of serum (FIGS. 7 and 8). To gain direct evidence that suppression of PKK expression leads to cell death of GCB DLBCL cells when they were cultured at low concentrations of serum, we analyzed the cell death by the Annexin V assay. As shown in FIG. 6C, SUDHL-6 cells that express either the control shRNA (shControl) or a PKK-specific shRNA (shPKK-1 or shPKK-2) yielded similar fractions of annexin V-positive cells when cultured in the medium containing 10% serum. In contrast, the cells that express an shPKK exhibited much higher fractions of annexin V-positive cells than the control cells when they were cultured under the serum-free condition. In addition, PKK knockdown resulted in marked increases in the cleavage of PARP and activation of caspase-3 in SUDHL-6 cells when they were cultured without serum (FIG. 6D). Thus, PKK is crucial for the survival of GCB DLBCL cells under certain conditions such as low serum conditions.

Example 4

Requirement for PKK in Tumor Growth from Xenografted GCB DLBCL Cells

Figure 9:
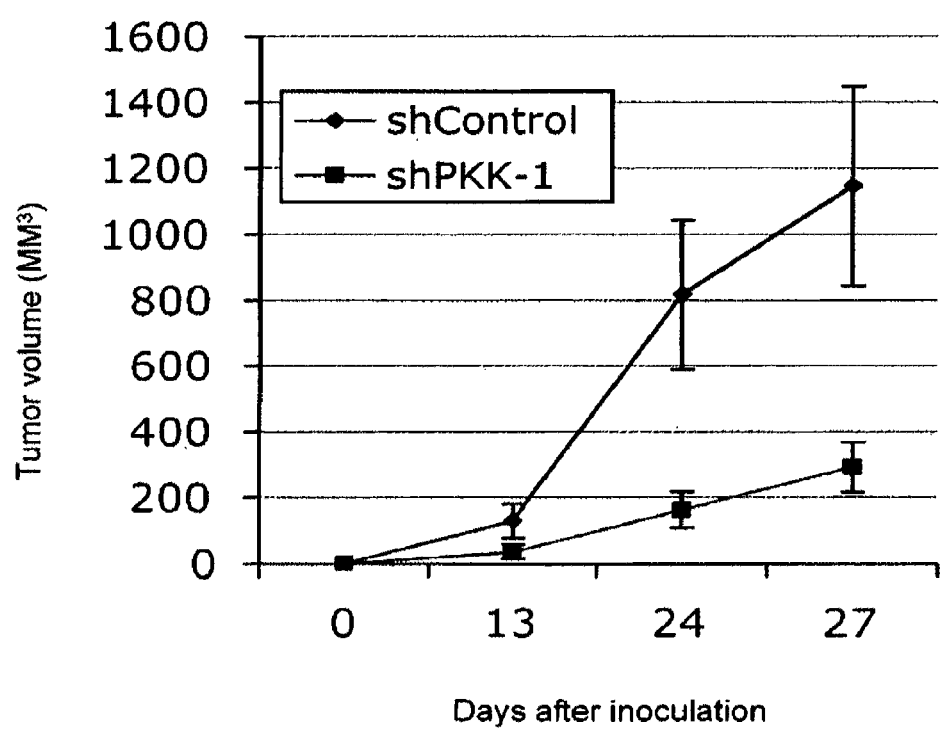
FIG. 9 shows that suppression of PKK expression inhibits tumor growth of xenografted OCI-Ly7 cells in NOD/SCID mice. OCI-Ly7 cells expressing shControl or shPKK-1 were injected subcutaneously into NOD/SCID mice (n=4, each). The tumor volumes were measured at the indicated times. The average tumor volumes from four injected mice are shown. The tumors from cells expressing shControl are significantly larger than those from the cells expressing shPKK-1 ($p<0.01$ at day 27 post-implantation).

Since PKK knockdown affects the survival of DLBCL cells in vitro, whether PKK is also required for the growth of these cells in vivo was examined. This issue was addressed by examining the effect of PKK knockdown on tumor growth of DLBCL cells in immunodeficient mice. SUDHL-6 cells were unable to form tumors in NOD/SCID mice upon subcutaneous inoculation under the experimental conditions utilized. Therefore, the focus was on tumor formation of xenografted OCI-Ly7 cells. Tumor growth was readily observed when OCI-Ly7 cells expressing the shControl were inoculated into the NOD/SCID mice. In contrast, the tumor growth of the OCI-Ly7 cells expressing shPKK-1 was significantly inhibited (FIG. 9). Thus, PKK is also required for tumor growth of OCI-Ly7 cells in vivo. This supports the belief that inhibiting the activity of PKK, or expression levels thereof, can diminish the survival of lymphoma B cells in whole animals.

Example 5

Knockdown of PKK Expression Sensitizes DLBCL Cells to Treatment with Chemotherapeutic Agents NF-κB activity protects cancer cells from apoptosis induced by chemotherapeutic agents and contributes to the resistance of malignant cells to chemotherapeutic agents (Kim et al., "NF-κB and IKK as Therapeutic Targets in Cancer," *Cell Death Differ* 13(5):738-47 (2006); Karin, "Nuclear Factor-κB in Cancer Development and Progression," *Nature* 441:431-436 (2006), each of which is hereby incorporated by reference in its entirety). As the results presented in Examples 1-4 demonstrate that PKK plays a critical role in NF-κB activation in DLBCL cells, it was reasoned that suppression of PKK expression might sensitize these cells to treatment by chemotherapeutic agents. To test this idea directly, SUDHL-6 cells expressing the shControl or an shPKK were treated with various concentrations of etoposide, a chemotherapeutic agent used in treatment of B-cell lymphoma (Gregory et al., "Chemotherapy Dose Intensity in Non-Hodgkin's Lymphoma: Is Dose Intensity an Emerging Paradigm for Better Outcomes?," *Ann Oncol* 16:1413-1424 (2005); Zelenetz et al., "Ifosfamide, Carboplatin, Etoposide (ICE)-based Second-line Chemotherapy for the Management of Relapsed and Refractory Aggressive Non-Hodgkin'S Lymphoma," *Ann Oncol* 14 Suppl 1:15-10 (2003), each of which is hereby incorporated by reference in its entirety).

Figures 10A, 10B:
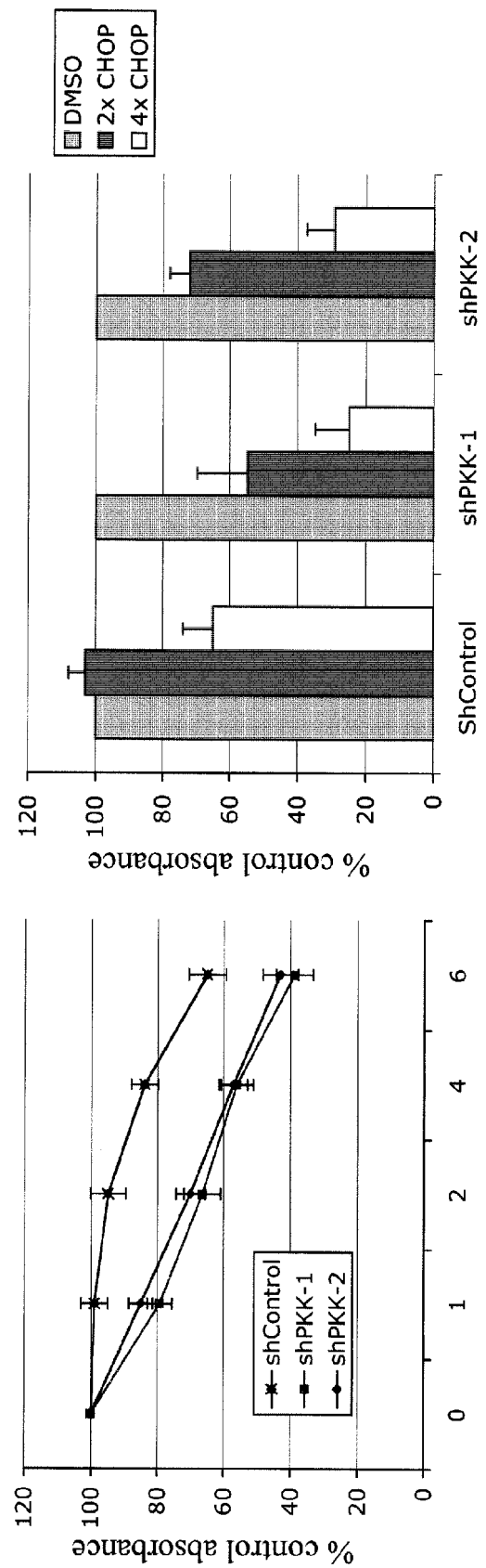
FIGS. 10A-B show that suppression of PKK expression sensitizes DLBCL cells to treatment with chemotherapeutic agents.

As shown in FIG. 10A, PKK knockdown increased the sensitivity of SUDHL-6 cells to etoposide treatment. To determine whether the increased sensitivity by PKK knockdown is specific for etoposide or common to other chemotherapeutic agents, the cells were also treated with CHOP (a combination of cyclophosphamide, doxorubicin, vincristine and prednisone), which has been widely used as the standard treatment for DLBCLs, were also treated (Abramson et al., Advances in the Biology and Therapy of Diffuse Large B-cell Lymphoma: Moving Toward a Molecularly Targeted Approach," *Blood* 106:1164-1174 (2005); Fisher, "Treatment of Diffuse Large B-cell Lymphomas," *Semin Hematol* 43:205-206 (2006); Coiffier, "State-of-the-art Therapeutics: Diffuse Large B-cell Lymphoma," *J Clin Oncol* 23:6387-6393 (2005), each of which is hereby incorporated by reference in its entirety). Similar to the response to etoposide, SUDHL-6 cells expressing shPKK exhibited increased sensitivity to CHOP treatment (FIG. 10B). Thus, inhibition of PKK expression sensitizes SUDHL-6 cells to treatment by multiple chemotherapeutic agents. These results suggest that PKK may contribute to the resistance of DLBCL cells to chemotherapeutic agents and inhibition of PKK may increase the efficacy of chemotherapy of DLBCL. These results also support the belief that more effective treatment of B cell lymphomas can be achieved by using an inhibitor of PKK activity in combination with chemotherapeutic agent(s), radiation therapy, and/or immunotherapy agents.

Example 6

Figure 11:
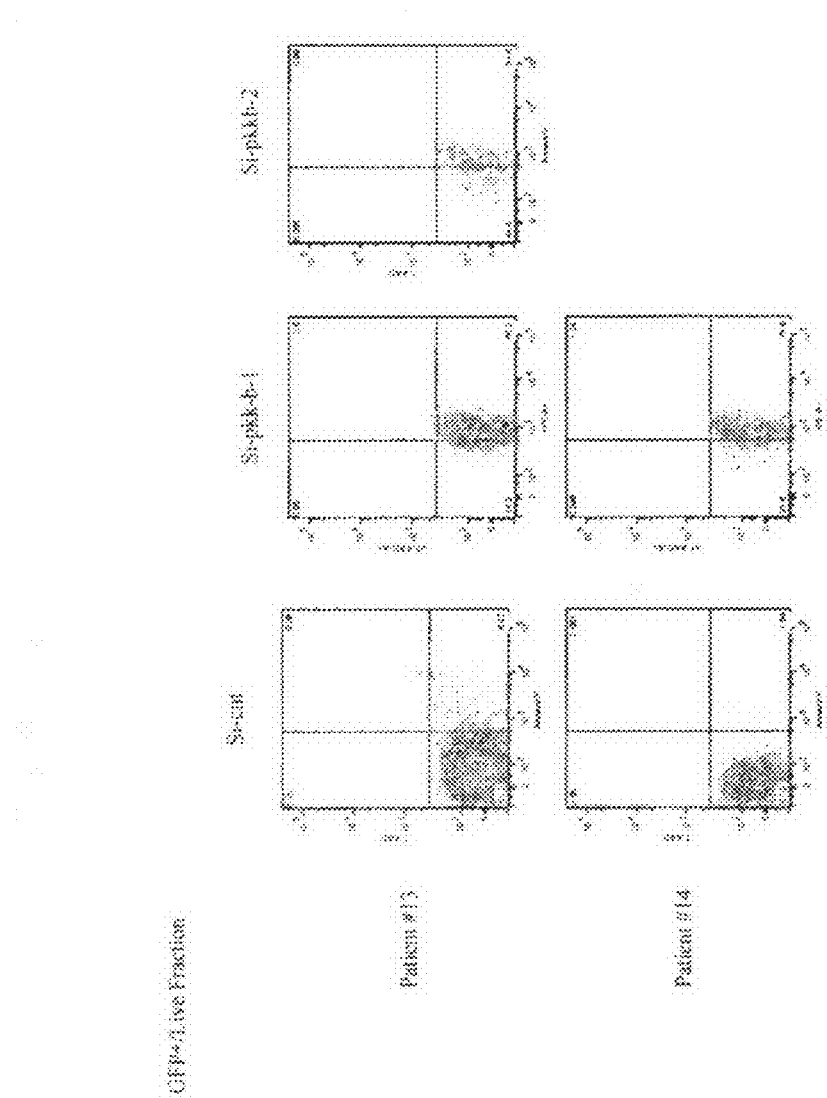
FIG. 11 shows the effect of suppression of PKK expression on survival of primary B-lymphoma cells. Primary B-lymphoma cells from DLBCL samples were infected with control lentivirus or lentiviruses expressing an shPKK as indicated. Two days after infection, cells were stained with Annexin V and 7-AAD, and analyzed by FACS. Analysis of infected (GFP-positive) cell populations are shown.

PKK is Required for Tumor Cell Survival and Proliferation of Primary DLBCL Cells The requirement for PKK by primary DLBCL cells was also analyzed. As shown in FIG. 11, primary DLBCL cells that were infected with lentiviruses expressing an shPKK showed significant higher apoptotic fractions that the cells infected with the lentivirus expressing a control shRNA. Thus, PKK is also required for the survival of primary DLBCL cells.

Example 7

Figure 12:
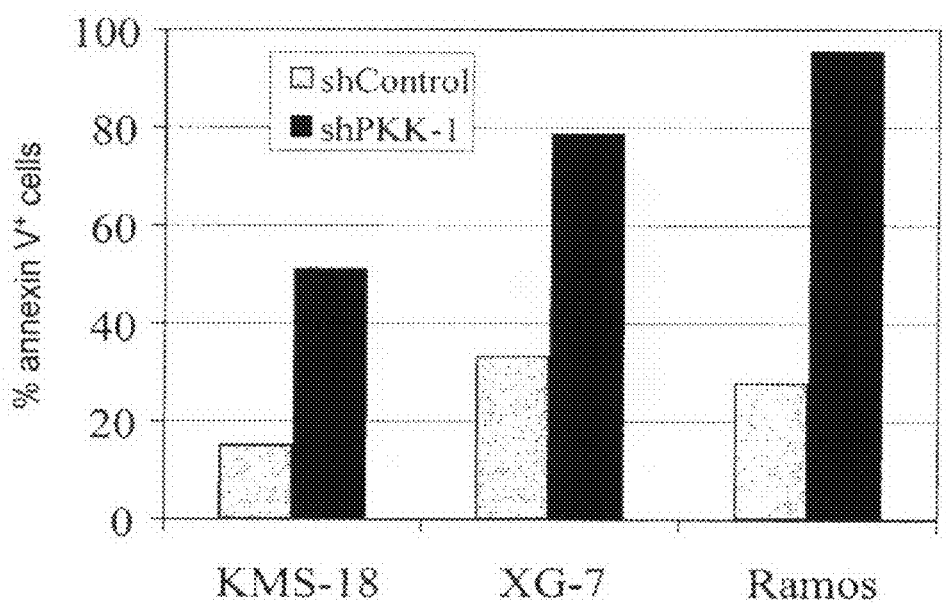
FIG. 12 shows that PKK knockdown induces apoptosis of multiple myeloma and Burkitt's lymphoma cells. Multiple myeloma cells (KMS-18 and XG-7) and Ramos Burkitt's lymphoma cells were infected with lentivirus expressing either a control shRNA (shControl) or a PKK-specific shRNA (shPKK-1), together with the GFP protein. Forty-eight hours after infection, cell death (apoptosis) of the infected cells (GFP positive) was analyzed using the annexin V-apoptosis detection kit (BD Bioscience).

PKK Knockdown Induces Apoptosis of Multiple Myeloma and Burkitt's Lymphoma Cells To explore whether PKK is required for the survival other malignant B-cells in addition to DLBCL cells, the effect of PKK knockdown on the survival of multiple myeloma and Burkitt's lymphoma cells was investigated. These two types of malignant B cells were chosen for testing because it was previously shown that aberrantly activated NF-κB signaling plays a crucial role in the survival of these malignant B cells (Annunziata et al., "Frequent Engagement of the Classical and Alternative NF-κB Pathways by Diverse Genetic Abnormalities in Multiple Myeloma," *Cancer Cell* 12(2):115-30 (2007); Keats et al., "Promiscuous Mutations Activate the Noncanonical NF-κB Pathway in Multiple Myeloma," *Cancer Cell* 12(2):131-44 (2007); Piva et al., "15-Deoxy-delta 12,14-prostaglandin J2 induces apoptosis in human malignant B cells: an effect associated with inhibition of NF-κB activity and down-regulation of antiapoptotic proteins," *Blood* 105(4):1750-1758 (2005), each of which is hereby incorporated by reference in its entirety). As shown in FIG. 12, PKK knockdown induced apoptosis in multiple myeloma and Burkitt's lymphoma cells. Thus, PKK is required for the survival of multiple types of malignant B cells.

Discussion of Examples 1-7

It was shown that PKK regulates constitutive NF-κB activity as well as NF-κB activation induced by BAFF in DLBCL cells. Notably, it was shown that PKK plays a crucial role in the survival of DLBCL cells, Burkitt's lymphoma cells, primary lymphoma cells, and myeloma cells.

All together, four primary B-lymphoma samples from four different patients (two Diffuse Large B cell Lymphoma tumors, and two follicular lymphoma tumors) have been tested. The data provides the same conclusion in that PKK is required for primary tumor cell survival and proliferation. Tumor cell lines that have been tested include 5 Diffuse Large B cell lymphoma cell lines: OCI-LY10, OCI-LY3, OCI-LY7, OCI-LY19 and SUD-HL6, one Burkitt's lymphoma line: Ramos, and two multiple myeloma cell lines: KMS-18 and XG-7. These tumor cell lines also support the conclusion that PKK is required for tumor cell survival/proliferation. Lastly, human blood cells (B cells are roughly 5% in the blood) infected with viruses expressing an shPKK were not apoptotic after 7 days (by FACS analysis), indicating that knocking down PKK has no effect for normal blood cell survival. Moreover, it was demonstrated that PKK is required for the growth of the DLBCL cells implanted in mice. In addition, it was further shown that suppression of PKK expression renders DLBCL cells more sensitive to treatment with chemotherapeutic agents. Therefore, PKK plays a critical role in NF-κB signaling and survival in several types of malignant B cells and may thus represent a promising drug target for treatment of B-cell malignancies.

It was previously shown that survival of the ABC subgroup of DLBCL cells, but not the GCB subgroup, requires constitutive NF-κB activity when the cells were cultured under normal in vitro growth conditions (Lam et al., "Small Molecule Inhibitors of IκB Kinase Are Selectively Toxic for Subgroups of Diffuse Large B-cell Lymphoma Defined by Gene Expression Profiling," *Clin Cancer Res* 11:28-40 (2005); Davis et al., "Molecular Diagnosis of Lymphoid Malignancies by Gene Expression Profiling," *Curr Opin Hematol* 9:333-338 (2002), each of which is hereby incorporated by reference in its entirety). Consistent with these earlier findings, it was observed that PKK is essential for the survival of OCI-Ly3 and OCI-Ly10 cells, two ABC DLBCL cell lines (FIGS. 4 and 5), but is dispensable for the survival of GCB DLBCL cells such as SUDHL-6 and OCI-Ly7 cells in medium with high concentrations of serum (FIG. 6A). Interestingly, these studies have uncovered that PKK, however, is required for the survival of GCB DLBCL cells under lower serum conditions and is essential for the growth of these cells in mice (FIGS. 6B-D and 9). These results extend previous observations and suggest that NF-κB activity also plays an important role in the survival of GCB DLBCL cells. Indeed, the preliminary results indicate that knockdown of IKKβ compromises the survival of GCB DLBCL cells under low serum conditions. Thus, GCB DLBCL subgroup may also be susceptible to the treatment with inhibitors of NF-κB signaling in vivo.

Constitutive NF-κB activity not only contributes to tumorigenesis but also promotes resistance to cancer therapy. Hence, inhibition of NF-κB signaling holds great potential for cancer therapy (Kim et al., "NF-κB and IKK as Therapeutic Targets in Cancer," *Cell Death Differ* 13(5):738-47 (2006); Karin, "Nuclear Factor-κB in Cancer Development and Progression," *Nature* 441:431-436 (2006); Karin et al., "The IKK NF-κB System: A Treasure Trove for Drug Development," *Nat Rev Drug Discov* 3:17-26 (2004), each of which is hereby incorporated by reference in its entirety). However, non-selective inhibition of NF-κB activity would likely cause serious side effects, as NF-κB activity is involved in various normal cellular functions. Thus, signaling molecules that regulate NF-κB activation specifically in cancer cells may represent superior targets for cancer chemotherapy. Mice deficient in PKK exhibit no apparent defects in B cell development, indicating that PKK is dispensable for normal B cell development. PKK knockdown caused no adverse effects on normal circulating B cells. Using shRNAs targeting multiple distinct human PKK sequences, it is shown here that PKK plays a crucial role in NF-κB activation and survival in lymphoma and myeloma cells. Thus, PKK may have acquired a critical role specifically in lymphoma and myeloma cells, while it has only limited roles in the development of normal B cells.

Emerging evidence indicates that BAFF plays a pivotal role in the survival of a variety of malignant B lymphocytes (Sutherland et al., "Targeting BAFF: Immunomodulation for Autoimmune Diseases and Lymphomas," *Pharmacol Ther* 112:774-786 (2006); Mackay et al., "The Role of the BAFF/APRIL. System in B Cell Homeostasis and Lymphoid Cancers," *Curr Opin Pharmacol* 4:347-354 (2004), each of which is hereby incorporated by reference in its entirety). Molecular understanding of BAFF signaling pathway may identify effective drug targets for the treatment of B-cell lymphomas. The above Examples show that suppression of PKK inhibits NF-κB activation induced by BAFF in DLBCL cells (FIGS. 2 and 3). Thus, PKK may be an important player in BAFF signaling in malignant B cells. It is known that BAFF induces NF-κB activation through both the canonical and the alternative pathways (Kayagaki et al., "BAFF/BLyS Receptor 3 Binds the B Cell Survival Factor BAFF Ligand Through a Discrete Surface Loop and Promotes Processing of NF-κB2," *Immunity* 17:515-524 (2002); Claudio et al., "BAFF-induced NEMO-independent Processing of NF-κB2 in Maturing B cells," *Nat Immunol* 3:958-965 (2002); Schneider, P., "The Role of APRIL and BAFF in Lymphocyte Activation," *Curr Opin Immunol* 17:282-289 (2005); Sutherland et al., "Targeting BAFF: Immunomodulation for Autoimmune Diseases and Lymphomas," *Pharmacol Ther* 112:774-786 (2006); Hatada et al., "NF-κB1 p50 is Required for BLyS Attenuation of Apoptosis but Dispensable for Processing of NF-κB2 p100 to p52 in Quiescent Mature B Cells," *J Immunol* 171:761-768 (2003), each of which is hereby incorporated by reference in its entirety). The data clearly show that PKK is required for the activation of the classical NF-κB pathway induced by BAFF (FIG. 2), whether PKK also regulates the activation of the alternative NF-κB pathway induced by BAFF is less clear. Preliminary evidence has shown that suppression of PKK expression apparently inhibited generation of p52 from p100 after BAFF stimulation, suggesting that PKK may also be involved in the activation of the alternative pathway. However, it is not clear whether the observed inhibition of p52 production resulted from the direct inhibition of p100 processing or indirectly from the inhibition of p100 expression, as expression of p100 is positively regulated by the classic NF-κB pathway (Lombardi et al., "Structural and Functional Characterization of the Promoter Regions of the NFκB2 Gene," *Nucleic Acids Res* 23:2328-2336 (1995), which is hereby incorporated by reference in its entirety), and suppression of PKK inhibited p100 expression (FIG. 1).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of treating B-cell malignancies comprising: administering to a patient an amount of an inhibitor of protein kinase C-associated kinase (PKK) activity that is effective to cause cell death of a B cell malignancy, thereby treating the B-cell malignancy, wherein the inhibitor of PKK activity is an inhibitory RNA (RNAi) molecule or DNA molecule encoding the RNAi molecule, and the B cell malignancy is selected from the group consisting of diffuse large B cell lymphoma, Burkitt's lymphoma, follicular lymphoma, and multiple myeloma.

2. The method according to claim 1, wherein the RNAi molecule interferes with PKK expression to cause a reduction in PKK activity.

3. The method according to claim 1, wherein the DNA molecule is present in an expression vector.

4. The method according to claim 1, wherein the RNAi molecule is an shRNA molecule selected from the group of:

| | |
|---|---|
| GGCCCACCTTCCAAGAAATTA, | (SEQ ID NO: 10) |
| CGTTCGTTTCTCGTTGCCTAA, and | (SEQ ID NO: 11) |
| GCACGATGTATACAGCTTTGC. | (SEQ ID NO: 12) |

5. The method according to claim 1, wherein said administering is carried out orally, parenterally, subcutaneously, intravenously, intramuscularly, intraperitoneally, by intranasal instillation, by implantation, by intracavitary or intravesical instillation, intraocularly, intraarterially, intralesionally, transdermally, by application to mucous membranes, or by introduction into one or more lymph nodes.

6. The method according to claim 1 further comprising administering an additional therapeutic agent selected from the group of a chemotherapeutic, radiation therapy, immunotherapy, and combinations thereof.

7. The method according to claim 1, wherein the B cell malignancy is diffuse large B cell lymphoma.

8. The method according to claim 1, wherein the B cell malignancy is Burkitt's lymphoma.

9. The method according to claim 1, wherein the B cell malignancy is follicular lymphoma.

10. The method according to claim 1, wherein the B cell malignancy is multiple myeloma.

\* \* \* \* \*

SEQUENCE LISTING

```
<160> NUMBER OF SEQ ID NOS: 15

<210> SEQ ID NO 1
<211> LENGTH: 21
<212> TYPE: DNA
<213> ORGANISM: Artificial
<220> FEATURE:
<223> OTHER INFORMATION: siRNA target of human PKK

<400> SEQUENCE: 1
aagaacatcc tgcacatcat g                                                 21

<210> SEQ ID NO 2
<211> LENGTH: 21
<212> TYPE: RNA
<213> ORGANISM: Artificial
<220> FEATURE:
<223> OTHER INFORMATION: siRNA sense strand, targeting SEQ ID NO: 1

<400> SEQUENCE: 2
aagaacaucc ugcacaucau g                                                 21

<210> SEQ ID NO 3
<211> LENGTH: 21
<212> TYPE: RNA
<213> ORGANISM: Artificial
<220> FEATURE:
<223> OTHER INFORMATION: siRNA antisense strand, targeting SEQ ID NO: 1

<400> SEQUENCE: 3
caugaugugc aggauguucu u                                                 21

<210> SEQ ID NO 4
<211> LENGTH: 21
<212> TYPE: DNA
<213> ORGANISM: Artificial
<220> FEATURE:
```

```
<223> OTHER INFORMATION: siRNA target of human PKK

<400> SEQUENCE: 4
aagaagatgg agatggccaa g                                              21

<210> SEQ ID NO 5
<211> LENGTH: 21
<212> TYPE: RNA
<213> ORGANISM: Artificial
<220> FEATURE:
<223> OTHER INFORMATION: siRNA sense strand, targeting SEQ ID NO: 4

<400> SEQUENCE: 5
aagaagaugg agauggccaa g                                              21

<210> SEQ ID NO 6
<211> LENGTH: 21
<212> TYPE: RNA
<213> ORGANISM: Artificial
<220> FEATURE:
<223> OTHER INFORMATION: siRNA antisense strand, targeting SEQ ID NO: 4

<400> SEQUENCE: 6
cuuggccauc uccaucuucu u                                              21

<210> SEQ ID NO 7
<211> LENGTH: 21
<212> TYPE: DNA
<213> ORGANISM: Artificial
<220> FEATURE:
<223> OTHER INFORMATION: siRNA target of human PKK

<400> SEQUENCE: 7
aaccttcaac cagcgatctg g                                              21

<210> SEQ ID NO 8
<211> LENGTH: 21
<212> TYPE: RNA
<213> ORGANISM: Artificial
<220> FEATURE:
<223> OTHER INFORMATION: siRNA antisense strand, targeting SEQ ID NO: 7

<400> SEQUENCE: 8
aaccuucaac cagcgaucug g                                              21

<210> SEQ ID NO 9
<211> LENGTH: 21
<212> TYPE: RNA
<213> ORGANISM: Artificial
<220> FEATURE:
<223> OTHER INFORMATION: siRNA antisense strand, targeting SEQ ID NO: 7

<400> SEQUENCE: 9
ccagaucgcu gguugaaggu u                                              21

<210> SEQ ID NO 10
<211> LENGTH: 21
<212> TYPE: DNA
<213> ORGANISM: Artificial
<220> FEATURE:
<223> OTHER INFORMATION: sequence encoding shRNA designated shPKK-1

<400> SEQUENCE: 10
ggcccacctt ccaagaaatt a                                              21

<210> SEQ ID NO 11
```

```
<211> LENGTH: 21
<212> TYPE: DNA
<213> ORGANISM: Artificial
<220> FEATURE:
<223> OTHER INFORMATION: sequence encoding shRNA designated shPKK-2

<400> SEQUENCE: 11
cgttcgtttc tcgttgccta a                                         21

<210> SEQ ID NO 12
<211> LENGTH: 21
<212> TYPE: DNA
<213> ORGANISM: Artificial
<220> FEATURE:
<223> OTHER INFORMATION: sequence encoding shRNA designated shPKK-3

<400> SEQUENCE: 12
gcacgatgta tacagctttg c                                         21

<210> SEQ ID NO 13
<211> LENGTH: 23
<212> TYPE: DNA
<213> ORGANISM: Artificial
<220> FEATURE:
<223> OTHER INFORMATION: sequence encoding random shRNA control

<400> SEQUENCE: 13
gttctccgaa cgaacgtgtc acg                                       23

<210> SEQ ID NO 14
<211> LENGTH: 21
<212> TYPE: DNA
<213> ORGANISM: Artificial
<220> FEATURE:
<223> OTHER INFORMATION: PKK primer

<400> SEQUENCE: 14
atggagggcg acggcgggac c                                         21

<210> SEQ ID NO 15
<211> LENGTH: 20
<212> TYPE: DNA
<213> ORGANISM: Artificial
<220> FEATURE:
<223> OTHER INFORMATION: PKK primer

<400> SEQUENCE: 15
cagggagccc gtctccatgt                                           20
```